United States Patent [19]  [11] 4,180,657
Sih  [45] Dec. 25, 1979

[54] ACYL-SUBSTITUTED PHENYL ESTERS OF PROSTACYCLIN-TYPE COMPOUNDS

[75] Inventor: John C. Sih, Kalamazoo, Mich.

[73] Assignee: The Upjohn Company, Kalamazoo, Mich.

[21] Appl. No.: 933,329

[22] Filed: Aug. 14, 1978

[51] Int. Cl.² .................. C07D 307/93; C07D 311/94
[52] U.S. Cl. .................................... 542/426; 542/429; 260/346.22; 260/345.2
[58] Field of Search ........................ 260/345.2, 346.22; 542/426, 429

[56] References Cited
PUBLICATIONS

Johnson, J.A.C.S., 99:12, Jun. 1977.

Primary Examiner—John M. Ford
Assistant Examiner—Bernard Dentz
Attorney, Agent, or Firm—Morris L. Nielsen

[57] ABSTRACT

Acyl-substituted phenyl esters of prostacyclin-type compounds, for example the 4-acetylphenyl ester of prostacyclin ($PGI_2$) illustrated by the formula

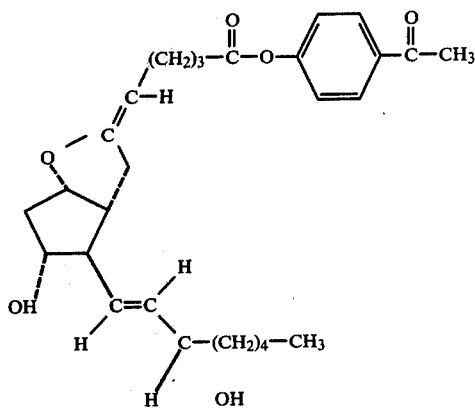

and including esters of the isomeric 6-hydroxy-$PGI_1$ and 6-keto-$PGF_1\alpha$ compounds, said esters having pharmacological activity. Processes for preparing them and the appropriate intermediates are disclosed.

63 Claims, No Drawings

ACYL-SUBSTITUTED PHENYL ESTERS OF PROSTACYCLIN-TYPE COMPOUNDS

BACKGROUND OF THE INVENTION

This invention relates to esters of prostacyclin-type compounds and to processes for preparing them.

Prostacyclin and prostacyclin-type compounds are well-known organic compounds. Prostacyclin ($PGI_2$) is represented by the formula:

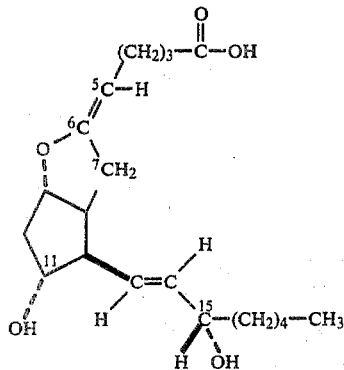

for which see R. A. Johnson, et al., J. Am. Chem. Soc. 99, 4182 (1977). Other prostacyclin-type compounds are disclosed by R. A. Johnson, et al., Prostaglandins 15, No. 5, 737–740 (1978) and in Belg. Pat. Nos. 851,122, 855,224, 859,057, and 860,278. See, respectively, Derwent Farmdoc Abstract Nos. 57511Y, 86540Y, 25186A, and 32096A.

These prostacyclin-type compounds are related to the well-known prostaglandins, including $PGF_{2\alpha}$ which is represented by the formula:

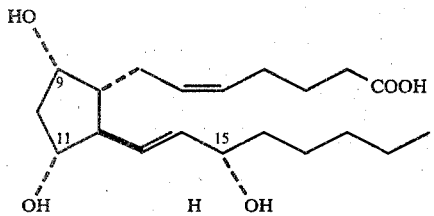

The prostaglandins are related to prostanoic acid which has the following structure and atom numbering:

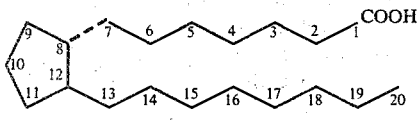

For background as to prostaglandins, see for example Bergstrom et al., Pharmacol. Rev. 20, 1 (1968); as to prostacyclin see S. Bunting, et al., Prostaglandins 12, No. 6, 897 (1976) and R. A. Johnson, et al., ibid 12, No. 6, 915 (1976); as to 6-keto-$PGF_{1\alpha}$, see Pace-Asciak, J. Am. Chem. Soc. 98, 2348 (1976). For acetylphenyl esters of certain prostaglandins, see W. Morozowich, U.S. Pat. Nos. 3,890,372 and 3,894,062.

As drawn hereinafter the formulas represents a particular optically active isomer having the same absolute configuration as $PGE_1$ obtained from mammalian tissues or $PGI_2$ obtained from enzymatic transformation of prostaglandin endoperoxides.

In the formulas, broken line attachments to the cyclopentane ring or side chain indicate substituents in alpha configuration, i.e. below the plane of the ring or side chain. Heavy solid line attachments indicate substituents in beta configuration, i.e. above the plane.

For nomenclature of the prostaglandins, see for example N. A. Nelson, J. Medic. Chem. 17, 911 (1974); as to prostacyclins see Roy A. Johnson, et al., Prostaglandins 15, No. 5, 737–740 (1978). With respect to "R" and "S" usage, as for substitution at C-6 and C-15 herein, see R. S. Cahn, J. Chem. Ed. 41, 116 (1964). As to the "Z" and "E" nomenclature see J. E. Blackwood, et al., J. Am. Chem. Soc. 90, 509 (1968).

Certain of the compounds are named as "6-keto" or "6-hydroxy", "5-keto" or "5-hydroxy" and "5-halo" or "4-halo" depending on the carbon atoms between that group and the cyclopentane ring, regardless of variations in chain length between that group and the terminal carboxyl group. Those variations in chain length are identified in the name with "homo" or "nor".

Prostacyclin and prostacyclin-type compounds are known for their potency in causing various biological responses. For that reason, these compounds are useful for pharmacological purposes. A few of those biological responses are: inhibition of blood platelet aggregation, stiumulation of smooth muscle, inhibition of gastric secretion and reduction of undesirable gastrointestional effects from systemic administration of prostaglandin synthetase inhibitors.

Because of these biological responses, prostacyclin and prostacyclin-type compounds are useful to study, prevent, control, or alleviate a wide variety of diseases and undesirable physiological conditions in mammals, including humans, useful domestic animals, pets, and zoological specimens, and in laboratory animals, for example, mice, rats, rabbits, and monkeys.

Prostacyclin and prostacyclin-type compounds are useful whenever it is desired to inhibit platelet aggregation, to reduce the adhesive character of platelets, and to remove or prevent the formation of thrombi in mammals, including man, rabbits, and rats. For example, these compounds are useful in the treatment and prevention of myocardial infarcts, to treat and prevent post-operative surgery, and to treat conditions such as atherosclerosis, arteriosclerosis, blood clotting defects due to lipemia, and other clinical conditions in which the underlying etiology is associated with lipid imbalance or hyperlipidemia. Other in vivo applications include geriatric patients to prevent cerebral ischemic attacks and long term prophylaxis following myocardial infarcts and strokes. For these purposes, these compounds are administered systemically, e.g., intravenously, subcutaneously, intramuscularly, and in the form of sterile implants for prolonged action. For rapid response, especially in emergency situations, the intravenous route of administration is preferred. Doses in the range about 0.01 to about 10 mg. per kg. of body weight per day are used, the exact dose depending on the age, weight, and condition of the patient or animal, and on the frequency and route of administration.

The addition of prostacyclin and prostacyclin-type compounds to whole blood provides in vitro applications such as storage of whole blood to be used in heart-lung machines. Additionally whole blood containing these compounds can be circulated through limbs and organs, e.g. heart and kidneys, whether attached to the original body, detached and being preserved or prepared for transplant, or attached to a new body. Blocking of aggregated platelets is avoided by the presence of these compounds. For this purpose, the compound is added gradually or in single or multiple portions to the circulating blood, to the blood of the donor person or animal, to the perfused body portion, attached or detached, to the recipient, or to two or all of those at a total steady state dose of about 0.001–1.0 μg/ml. of whole blood. These compounds are also useful in preparing platelet-rich concentrates from blood for use in treating thrombocytopenia or in chemotherapy.

Prostacyclin and protacyclin-type compounds are extremely potent in causing stimulation of smooth muscle, and are also highly active in potentiating other known smooth muscle stimulators, for example, oxytocic agents, e.g., oxytocin, and the various ergot alkaloids including derivatives and analogs thereof. Therefore, they are useful in place of or in combination with less than usual amounts of these known smooth muscle stimulators, for example, to relieve the symptoms of paralytic ileus, or to control or prevent atonic uterine bleeding after abortion or delivery, to aid in expulsion of the placenta, and during the puerperium. For the latter purpose, the compound is administered by intravenous infusion immediately after abortion or delivery at a dose in the range about 0.01 to about 50 μg per kg. of body weight per minute until the desired effect is obtained. Subsequent doses are given by intravenous, subcutaneous, or intramuscular injection or infusion during puerperium in the range 0.01 to 2 mg. per kg. of body weight per day, the exact dose depending on the age, weight, and condition of the patient or animal.

Prostacyclin and prostacyclin-type compounds are also useful in mammals, including man and certain useful animals, e.g. dogs and pigs, to reduce and control excessive gastric secretion, thereby reduce or avoid gastrointestinal ulcer formation, and accelerate the healing of such ulcers already present in the gastrointestinal tract. For this purpose, these compounds are injected or infused intravenously, subcutaneously, or intramuscularly in an infusion dose range about 0.1 μg per kg. of body weight per minute, or in a total daily dose by injection or infusion in the range about 0.01 to about 10 mg. per kg. of body weight per day, the exact dose depending on the age, weight, and condition of the patient or animal, and on the frequency and route of administration.

Prostacyclin and prostacyclin-type compounds are also useful in reducing the undesirable gastrointestinal effects resulting from systemic administration of anti-inflammatory prostaglandin synthetase inhibitors, and are used for that purpose by concomitant administration of the prostacyclin or prostacyclin-type compound and the anti-inflammatory protaglandin synthetase inhibitor. The anti-inflammatory synthetase inhibitor, for example indomethacin, aspirin, or phenylbutazone is administered in any of the ways known in the art to alleviate an inflammatory condition, for example, in any dosage regimen and by any of the known routes of systemic administration. The prostacyclin or prostacyclin-type compound is administered along with the anti-inflammatory prostaglandin synthetase inhibitor either by the same route of administration or by a different route.

Prostacyclin or prostacyclin-type compounds are also useful in the treatment of asthma. For example, these compounds are useful as bronchodilators or as inhibitors of mediators, such as SRS-A, and histamine which are released from cells activated by an antigen-antibody complex. Thus, these compounds control spasm and facilitate breathing in conditions such as bronchial asthma, bronchitis, bronchiectasis, pneumonia and emphysema. For these purposes, these compounds are administered in a variety of dosage forms, e.g., orally in the form of tablets, capsules, or liquids, rectally in the form of suppositories, parenterally, subcutaneously, or intramuscularly, with intravenous administration being preferred in emergency situations, by inhalation administration being preferred in emergency situations, by inhalation in the form of aerosols or solutions for nebulizers; or by insufflation in the form of powder. Doses in the range of about 0.01 to 5 mg. per kg. of body weight are used 1 to 4 times a day, the exact dose depending on the age, weight, and condition of the patient and on the frequency and route of administration. For the above use the prostacyclin or prostacyclin-type compound can be combined advantageously with other anti-asthmatic agents, such as sympathomimetics (isoproterenol, phenylephrine, ephedrine, etc.); xanthine derivatives (theophylline and aminophylline); and corticosteroids (ACTH and prednisolone). Prostacyclin or prostacyclin-type compounds are effectively administered to human asthma patients by oral inhalation or by aerosol inhalation. For administration by the oral inhalation route with conventional nebulizers or by oxygen aerosolization it is convenient to provide the prostacyclin ingredient in dilute solution, preferably at concentrations of about 1 part of medicament to from about 100 to 200 parts by weight of total solution. Entirely conventional additives may be employed to stabilize these solutions or to provide isotonic media, for example, sodium chloride, sodium citrate, citric acid, and the like can be employed. For administration as a self-propelled dosage unit for administering the active ingredient in aerosol form suitable for inhalation therapy the composition can comprise the active ingredient suspended in an inert propellant (such as a mixture of dichlorodifluoromethane and dichlorotetrafluoroethane) together with a co-solvent, such as ethanol, flavoring materials and stabilizers. Instead of a co-solvent there can also be used a dispensing agent such as oleyl alcohol. Suitable means to employ the aerosol inhalation therapy technique are described fully in U.S. Pat. No. 2,868,691 for example.

Prostacyclin or prostacyclin-type compounds are useful in mammals, including man, as nasal decongestants and are used for this purpose in a dose range of about 10 μg. to about 10 mg. per ml. of a pharmacologically suitable liquid vehicle or as an aerosol spray, both for topical application.

Prostacyclin or prostacyclin-type compounds are also useful in treating peripheral vascular disease in humans. The term peripheral vascular disease as used herein means disease of any of the blood vessels outside of the heart and to disease of the lymph vessels, for example, frostbite, ischemic cerebrovascular disease, arteriovenous fistulas, ischemic leg ulcers, phlebitis, venous insufficiency, gangrene, hepatorenal syndrom, ductus arteriosus, non-obstructive mesenteric ischemia, arteritis lymphangitis and the like. These examples are included to be illustrative and should not be construed as limiting the term peripheral vascular disease. For these conditions the prostacyclin compounds are administered orally or parenterally via injection or infusion directly into a vein or artery. The dosages of these compounds are in the range of 0.01–1.0 μg. administered by infusions at an hourly rate or by injection on a daily basis, i.e. 1–4 times a day, the exact dose depending on the age, weight, and condition of the patient and on the frequency and route of administration. Treatment is continued for one to five days, although three days is ordinarily sufficient to assure long-lasting therapeutic action. In the event that systemic or side effects are observed the dosage is lowered below the threshold at which such systemic or side effects are observed. Prostacyclin or prostacyclin-type compounds are accordingly useful for treating peripheral vascular diseases in the extremities of humans who have circulatory insufficiencies in said extremities, such treatment affording relief of rest pain and induction of healing of ulcers. For a complete discussion of the nature of the clinical manifestations of human peripheral vascular disease and the method previously known of its treatment with prostaglandins see South African Pat. No. 74/0149 referenced as Derwent Farmdoc No. 58400V. See Elliott, et al., Lancet, Jan. 18, 1975, pp. 140–142.

Prostacyclin or prostacyclin-type compounds are useful in place of oxytocin to induce labor in pregnant female animals, including man, cows, sheep, and pigs, at or near term, or in pregnant animals with intrauterine death of the fetus from about 20 weeks to term. For this purpose, the compound is infused intravenously at a dose of 0.01 to 50 µg. per kg. of body weight per minute until or near the termination of the second stage of labor, i.e., expulsion of the fetus. These compounds are especially useful when the female is one or more weeks postmature and natural labor has not started, or 12 to 60 hours after the membranes have ruptured and natural labor has not yet started. An alternative route of administration is oral.

Prostacyclin or prostacyclin-type compounds are further useful for controlling the reproductive cycle in menstruating female mammals, including humans. By the term menstruating female mammals is meant animals which are mature enough to menstruate, but not so old that regular menstruation has ceased. For that purpose the prostacyclin compound is administered systemically at a dose level in the range 0.01 mg. to about 20 mg. per kg. of body weight of the female mammal, advantageously during a span of time starring approximately at the time of ovulation and ending approximately at the time of menses or just prior to menses. Intravaginal and intrauterine routes are alternate methods of administration. Additionally, expulsion of an embryo or a fetus is accomplished by similar administration of the compound during the first or second trimester of the normal mammalian gestation period.

Prostacyclin or prostacyclin-type compounds are further useful in causing cervical dilation in pregnant and non-pregnant female mammals for purposes of gynecology and obstetrics. In labor induction and in clinical abortion produced by these compounds, cervical dilation produced by these compounds is useful in assisting sperm movement to the uterus. Cervical dilation by prostacyclin compounds is also useful in operative gynecology such as D and C (Cervical Dilation and Uterine Curettage) where mechanical dilation may cause performation of the uterus, cervical tears, or infections. It is also useful for diagnostic procedures where dilation is necessary for tissue examination. For these purposes, the prostacyclin compound is administered locally or systemically. The prostacyclin compound, for example, is administered orally or vaginally at doses of about 5 to 50 mg. per treatment of an adult female human, with from one to five treatments per 24 hour period. Alternatively the compound is administered intramuscularly or subcutaneously at doses of about one to 25 mg. per treatment. The exact dosages for these purposes depend on the age, weight, and condition of the patient or animal.

Prostacyclin and prostacyclin-type compounds are further useful in domestic animals as in abortifacients (especially for feedlot heifers), as an aid to estrus detection, and for regulation or synchronization of estrus. Domestic animals include horses, cattle, sheep, and swine. The regulation or synchronization of estrus allows for more efficient management of both conception and labor by enabling the herdsman to breed all his females in short pre-defined intervals. This synchronization results in a higher percentage of live births than the percentage achieved by natural control. The prostacyclin compound is injected or applied in a feed at doses of 0.1–100 mg. per animal and may be combined with other agents such as steroids. Dosing schedules will depend on the species treated. For example, mares are given the prostacyclin compound 5 to 8 days after ovulation and return to estrus. Cattle are treated at regular intervals over a 3 week period to advantageously bring all into estrus at the same time.

Prostacyclin or prostacyclin-type compounds increase the flow of blood in the mammalian kidney, thereby increasing volume and electrolyte content of the urine. For that reason, these compounds are useful in managing cases of renal dysfunction, especially those involving blockage of the renal vascular bed. Illustratively, these compounds are useful to alleviate and correct cases of edema resulting, for example, from massive surface burns, and in the management of shock. For these purposes, these compounds are preferably first administered by intravenous injection at a dose in the range 10 to 1000 µg. per kg. of body weight or by intravenous infusion at a dose in the range 0.1 to 20 µg. per kg. of body weight per minute until the desired effect is obtained. Subsequent doses are given by intravenous, intramuscular, or subcutaneous injection or infusion in the range 0.05 to 2 mg. per kg. of body weight per day.

These prostacyclin or prostacyclin-type compounds are useful for treating proliferating skin diseases of man and domesticated animals, including psoriasis, atopic dermatitis, non-specific dermatitis, primary irritant contact dermatitis, allergic contact dermatitis, basal and squamous cell carcinomas of the skin, lamellar ichthyosis, epidermolytic hyperkeratosis, premalignant sun-induced keratosis, non-maligant keratosis, acne, and seborrheic dermatitis in humans and atopic dermatitis and mange in domesticated animals. These compounds alleviate the symptoms of these proliferative skin diseases: psoriasis, for example, being alleviated when a scale-free psoriasis lesion is noticeably decreased in thickness or noticeably but incompletely cleared or completely cleared. For those purposes, these compounds are applied topically as compositions including a suitable pharmaceutical carrier, for example as an ointment, lotion, paste, jelly, spray, or aerosol, using topical bases such as petrolatum, lanolin, polyethylene glycols, and alcohols. These compounds, as the active ingredients, constitute from about 0.1% to about 15% by weight of the composition, preferably from about 0.5% to about 2%. In addition to topical administration, injection may be employed, as intradermally, intra- or perilesionally, or subcutaneously, using appropriate sterile saline compositions.

Prostacyclin or prostacyclin-type compounds are useful as anti-inflammatory agents for inhibiting chronic inflammation in mammals including the swelling and other unpleasant effects thereof using methods of treatment and dosages generally in accord with U.S. Pat. No. 3,885,041, which patent is incorporated herein by reference.

Among the prostacyclin-type compounds, the 5-hydroxy compounds of $PGI_1$ and its analogs are useful for potentiating other known smooth muscle stimulators in the manner set forth above. The 6-alkoxy compounds of $PGI_1$ and its analogs are useful to reduce and control excessive gastric secretion in mammals, to reduce undesirable gastrointestinal effects resulting from systemic administration of antiinflammatory prostaglandin synthetase inhibitors, and as hypotensive agents to reduce blood pressure in mammals. The prostacyclin analogs with a $\Delta^7$ feature are useful as antiinflammatory agents in mammals in the manner set forth above.

The 6-(and 5-) keto-$PGF_1$ compounds and analogs are also useful for at least one of the above pharmacological purposes and are used in the same manner.

SUMMARY OF THE INVENTION

It is the purpose of this invention to provide novel products having pharmacological activity. It is a further purpose to provide a process for preparing these products and their intermediates. More specifically, there are provided acyl-substituted phenyl esters of prostacyclin-type compounds.

Accordingly, there is provided a prostacyclin-type acid ester of the formula

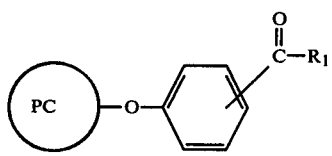

IV wherein $R_1$ is defined in the TABLE of Definition of Terms for Formulas, together with other terms used herein, and (PC) is a radical represented by loss of the carboxylic hydroxyl group from a prostacyclin-type compound of the group comprising (I) prostacyclin of the formula

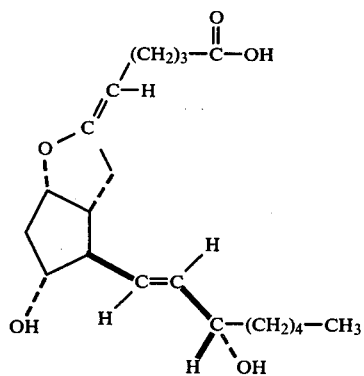

V or its (5E) isomer,
(II) prostacyclin analogs of the formula

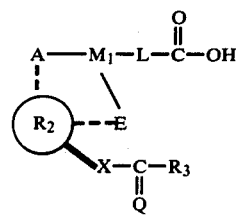

VI

TABLE
Definition of Terms for Formulas

A is
  (1) —O— (oxa) or, when E is —CH$_2$—, (2) —CH$_2$—O—, wherein —CH$_2$ is bonded to the cyclopentane ring.

E is
  —CH$_2$— or —CH$_2$CH$_2$—.

$L_1$ is
  (1) —(CH$_2$)$_n$— wherein n is one to 5, inclusive,
  (2) —(CH$_2$)$_p$—CF$_2$— wherein p is 2, 3, or 4, or
  (3) —(CH$_2$)$_v$—CH=CH— wherein v is 1, 2, or 3.

$M_1$ is

 (1)

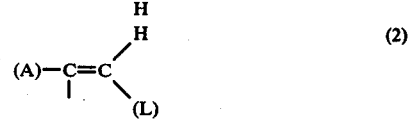 (2)

 (3)

or

 (4)

where ~ indicates attachment in alpha or beta configuration.

$M_2$ is

 (1)

or

 (2)

wherein ~ indicates attachment in cis or trans configuration.

$M_3$ is

 (1)

or

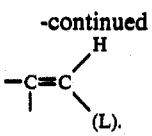
(2)

Q is

wherein R$_4$ is hydrogen or alkyl of one to 4 carbon atoms, inclusive.

R$_1$ is
alkyl of one to 4 carbon atoms, inclusive, with the proviso that when R$_1$ is tert-butyl the group

is only in the 4-position.

R$_2$ is

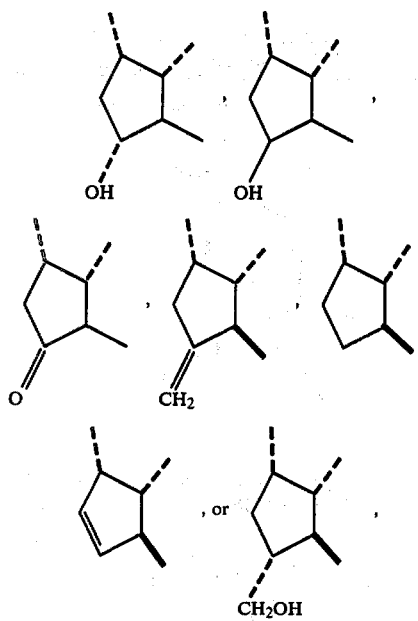

R$_3$ is

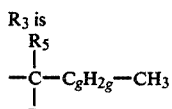 (1)

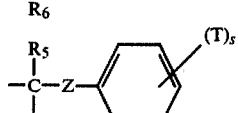 (2)

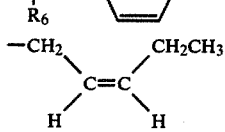 (3)

wherein C$_g$H$_{2g}$ is alkylene of one to 9 carbon atoms, inclusive, with one to 5 carbon atoms, inclusive, in the chain between —CR$_5$R$_6$— and terminal methyl, wherein R$_5$ and R$_6$ are hydrogen, alkyl of one to 4 carbon atoms, inclusive, or fluoro, being the same or different, with the proviso that one of R$_5$ and R$_6$ is fluoro only when the other is hydrogen or fluoro and the further proviso that neither R$_5$ nor R$_6$ is fluoro when Z is oxa (—O—);

wherein Z represents an oxa atom (—O—) or C$_j$H$_{2j}$ wherein C$_j$H$_{2j}$ is a valence bond or alkylene of one to 9 carbon atoms, inclusive, with one to 6 carbon atoms, inclusive between CR$_5$R$_6$— and the phenyl ring;

wherein T is alkyl of one to 4 carbon atoms; inclusive, fluoro, chloro, trifluoromethyl, or —OR$_7$— wherein R$_7$ is alkyl of one to 4 carbon atoms, inclusive, and s is zero, one, 2 or 3, with the proviso that not more than two T's are other than alkyl and when s is 2 or 3 the T's are either the same or different.

R$_4$ is
hydrogen or alkyl of one to 4 carbon atoms, inclusive.

R$_5$ and R$_6$ are
hydrogen, alkyl of one to 4 carbon atoms, inclusive, or fluoro, being the same or different, with the proviso that one of R$_5$ and R$_6$ is fluoro only when the other is hydrogen or fluoro and the further proviso that neither R$_5$ nor R$_6$ is fluoro when Z is (—O—).

R$_7$ is
alkyl of one to 4 carbon atoms, inclusive.

R$_8$ is

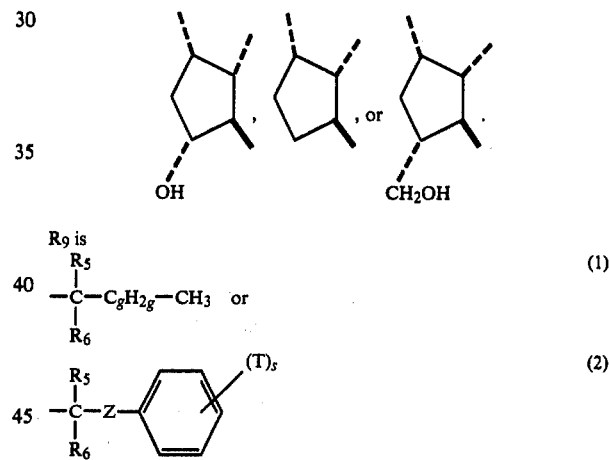

R$_9$ is (1)

(2)

wherein R$_5$, R$_6$, T, Z, s, and C$_g$H$_{2g}$ are as defined herein.

R$_{10}$ is
straight-chain alkyl of one to 6 carbon atoms, inclusive.

R$_{11}$ is
hydrogen, hydroxy, or hydroxymethyl.

R$_{12}$ is

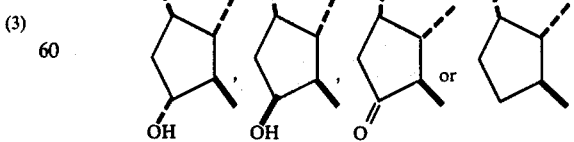

R$_{13}$ is
hydrogen or an alkali metal cation of the group consisting of sodium, potassium, and lithium.

R$_{14}$ is bromo or chloro.

T is
  alkyl of one to 4 carbon atoms; inclusive, fluoro, chloro, trifluoromethyl, or —OR$_7$— wherein R$_7$ is alkyl of one to 4 carbon atoms, inclusive, and s is zero, one, 2 or 3, with the proviso that not more than two T's are other than alkyl and when s is 2 or 3 the T's are either the same or different.

X is
  (1) trans-CH=CH—
  (2) cis-CH=CH—
  (3) —C≡C— or
  (4) —CH$_2$CH$_2$—.

Z is
  an oxa atom (—O—) or C$_j$H$_{2j}$ wherein C$_j$H$_{2j}$ is a valence bond or alkylene of one to 9 carbon atoms, inclusive, with one to 6 carbon atoms, inclusive between —CR$_5$R$_6$— and the phenyl ring.

C$_g$H$_{2g}$ is alkylene of one to 9 carbon atoms, inclusive, with one to 5 carbon atoms, inclusive, in the chain between —CR$_5$R$_6$— and terminal methyl.

C$_j$H$_{2j}$ is
  a valence bond or alkylene of one to 9 carbon atoms, inclusive, with one to 6 carbon atoms, inclusive between —CR$_5$R$_6$— and the phenyl ring.

n is
  one to 5, inclusive,
p is
  2, 3 or 4.
s is
  zero, one, 2 or 3.
v is
  one, 2 or 3.
w is
  one, 2 or 3.
~ indicates
  attachment in alpha or beta configuration.

END OF TABLE (III) prostacyclin analogs of the formula

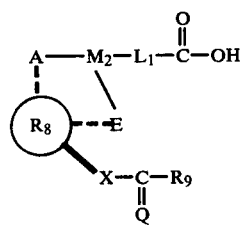

VII (IV) prostacyclin analogs of the formula

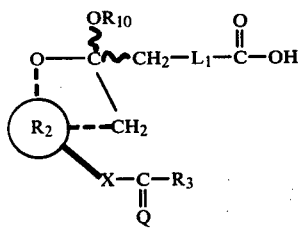

VIII (V) prostacyclin analogs of the formula

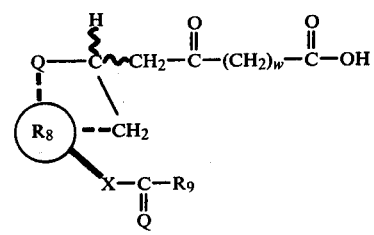

IX (VI) prostacyclin analogs of the formula

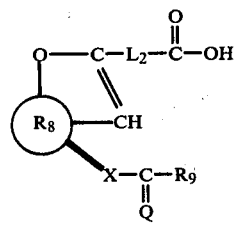

X (VII) prostacyclin analogs of the formula
(VII) prostacyclin analogs of the formula

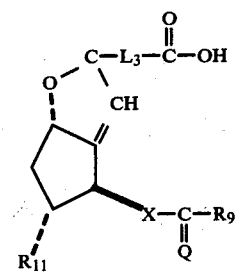

XI and (VIII) 6a-carba prostacyclin analogs of the formula

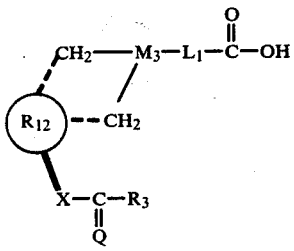

XII

The acyl-substituted phenoxy moiety of these esters which is represented by

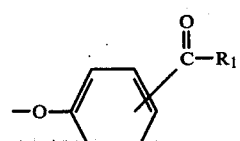

in formula IV includes, for example
(2,3 or 4)-acetylphenoxy
(2,3 or 4)-propionylphenoxy (2,3 or 4)-butyrylphenoxy
(2,3 or 4)-isobutyrylphenoxy
(2,3 or 4)-valerylphenoxy
(2,3 or 4)-isovalerylphenoxy and
4-pivalylphenoxy corresponding to an appropriate phenol, for example 2-acetylphenol, alternatively known as 2-hydroxyacetophenone or 1-(2-hydroxy)-phenylethanone.

The formula-VI compounds of group II above include

PGI$_2$ analogs, for example (5Z)-trans-$\Delta^2$-PGI$_2$,
(5E)-PGI$_2$ analogs, for example (5E)-11-deoxy-PGI$_2$,
PGI$_1$, analogs, for example (6S or 6R)-PGI$_1$,
6-hydroxy-PGI$_1$ analogs, for example 6$\xi$-6-hydroxy-PGI$_1$,
9-deoxy-5,9$\alpha$-epoxy-$\Delta^4$-PGF$_1$ analogs, for example (4Z)-9-deoxy-5,9$\alpha$-epoxy-$\Delta^4$-PGF$_1$,
9-deoxy-5,9$\alpha$-epoxy-PGF$_1$ compounds, for example (5S or 5R)-9-deoxy-5,9$\alpha$-epoxy-PGF$_1$,
5-hydroxy-9-deoxy-5,9$\alpha$-epoxy-PGF$_1$ analogs, for example 5$\xi$-5-hydroxy-9-deoxy-5,9$\alpha$-epoxy-PGF$_1$,
9-deoxy-6,9$\alpha$-epoxymethano-$\Delta^5$-PGF$_1$ analogs, for example (5Z)-9-deoxy-6,9$\alpha$-epoxymethano-$\Delta^5$-PGF$_1$,
9-deoxy-6,9$\alpha$-epoxymethano-PGF$_1$ analogs, for example (6S or 6R)-9-deoxy-6,9$\alpha$-epoxymethano-PGF$_1$, and
6-hydroxy-9-deoxy-6,9$\alpha$-epoxymethano-PGF$_1$ analogs, for example 6$\xi$-6-hydroxy-9-deoxy-6,9$\alpha$-epoxymethano-PGF$_1$.

The formula-VII compounds of Group III above include 5-hydroxy-PGI$_1$ analogs, for example (5S or 5R)-5-hydroxy-(6S)-PGI$_1$, and, trans-$\Delta^4$-PGI$_1$ analogs, for example trans-$\Delta^4$-(6R)-PGI.

The formula-VIII compounds of Group IV above include 6-alkoxy-PGI$_1$ analogs, for example (6S or 6R)-6-methoxy-PGI$_1$.

The formula-IX compounds of Group V above include 4-oxo-PGI$_1$ analogs, for example 4-oxo-(6R or 6S)-PGI$_1$.

The formula-X compounds of Group VI above include $\Delta^6$-PGI$_1$ analogs, for example $\Delta^6$-11-deoxy-11$\alpha$-11-hydroxymethyl-PGI$_1$.

The formula-XI compounds of Group VII above include $\Delta^7$-PGI$_1$ analogs, for example $\Delta^7$-(6R or 6S)-PGI$_1$.

The formula-XII compounds of Group VIII include 6a-carba-PGI$_2$ analogs, for example (5Z or 5E)-6a-carba-PGI$_2$.

In addition to the compounds of formula IV, i.e. prostacyclin-type acid esters, there are included in this invention acid esters of the formula

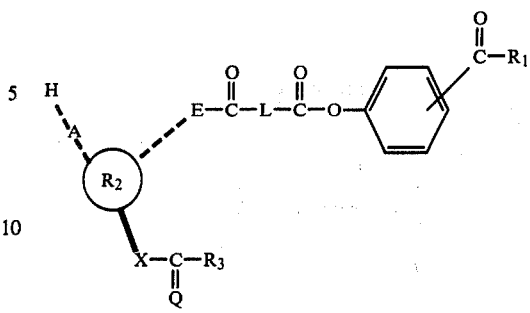

wherein the terms are as defined in the Table. These are included because they represent 6 (or 5)-keto prostaglandin compounds which are isomers of 6 (or 5)-hydroxy prostacyclin compounds within the scope of formula IV above. They are found in equilibrium with those compounds and, at least in solution, are always present together with their isomeric counterpart.

The formula-XIII compounds include 6-keto-PGF$_{1\alpha}$ analogs, for example 6-keto-PGF$_{1\alpha}$ and
6-keto-9-deoxy-9$\alpha$-hydroxymethyl-PGF$_1$ and
5-keto-PGF$_{1\alpha}$ analogs, for example 5-keto-PGF$_{1\alpha}$.

The novel formula-IV and -XIII compounds are each useful for the same purposes as described above for their respective parent acids and salts, and are used for those purposes in the same manner known in the art, including oral, sublingual, buccal, rectal, intravaginal, intrauterine, topical, or inhalation administration.

These acyl-substituted phenyl esters have advantages over the corresponding known prostacyclin or prostaglandin compounds in that they are more stable, they are often obtained in crystalline form for ease of handling, and have even shown greater efficacy than the corresponding free acids or salts. The crystalline esters also provide a means of purifying the prostacyclin or prostaglandin compound by recrystallization.

Reference to Charts A, B, C, and D, herein, will make clear the processes for preparing the compounds of this invention. In those charts (PC) has the same meaning as above, i.e. a radical corresponding to loss of the carboxylic hydroxyl group from a prostacyclin-type compound, and the terms A, E, etc. are as defined in the Table.

In Chart A the acid or alkali metal salt of a prostacyclin-type compound, for example the sodium salt of prostacyclin (PGI$_2$), (5E)-prostacyclin, or 6,7-didehydro-PGI$_1$, is converted to a mixed anhydride with isobutylchloroformate in the presence of a tertiary amine. Thereafter the anhydride is reacted with the phenol, for example 1-(2, 3, or 4-hydroxy)phenylethanone (alternatively "o, m, or p-hydroxyacetophenone"), in the presence of a tertiary amine. If the prostacyclin-type compound is of the PGI$_1$ class and accordingly more stable than the enol ethers such as PGI$_2$, the acid form is useful as starting material.

Among the formula-XIV prostacyclin-type compounds are:

I. Prostacyclin (PGI$_2$) and (5E)-prostacyclin. See Johnson, et al., J. Am. Chem. Soc. 99, 4182 (1977).

II. Prostacyclin analogs of formula VI, for which see Belg. Pat. No. 851,122, Derwent Farmdoc Abstracts No. 57511Y. Included are PGI$_2$ analogs, for example:

(5Z)-trans-$\Delta^2$-PGI$_2$
(5Z)-2,2-difluoro-PGI$_2$

CHART A
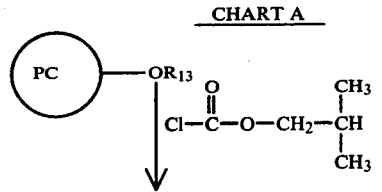
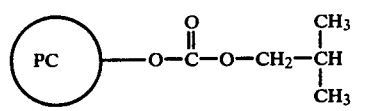
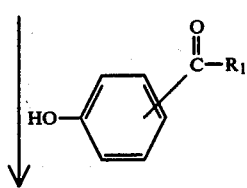
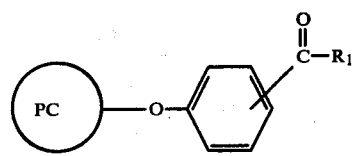
CHART B
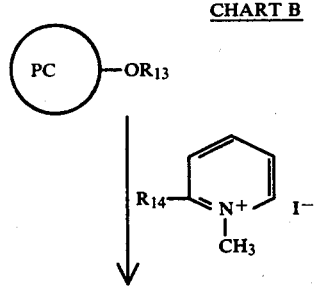
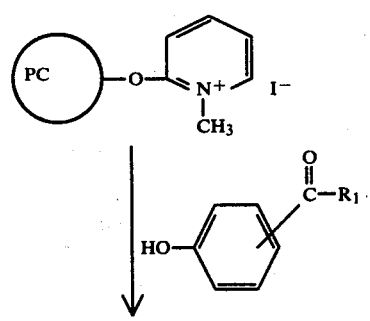
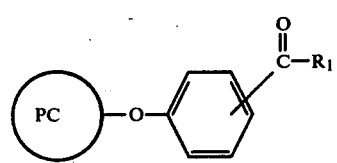
CHART C
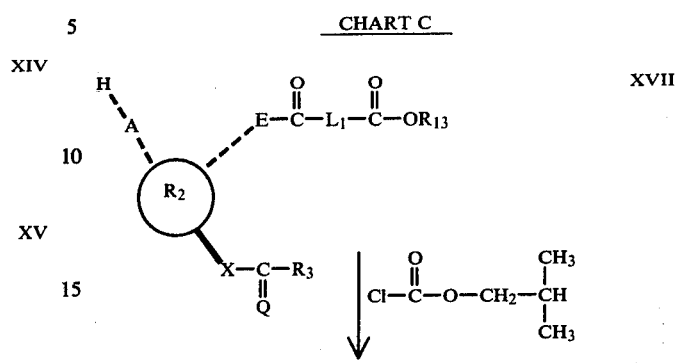
XIV
XVII
XVIII
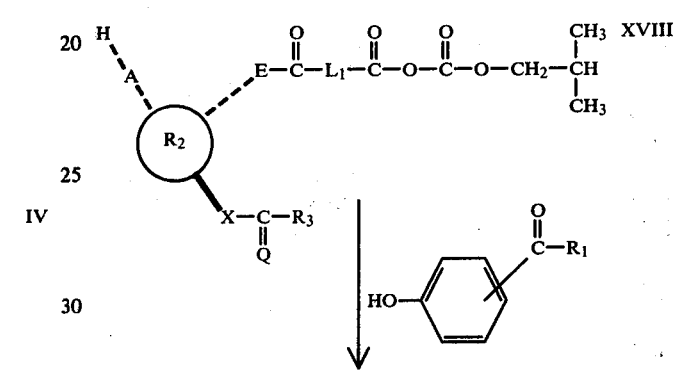
IV
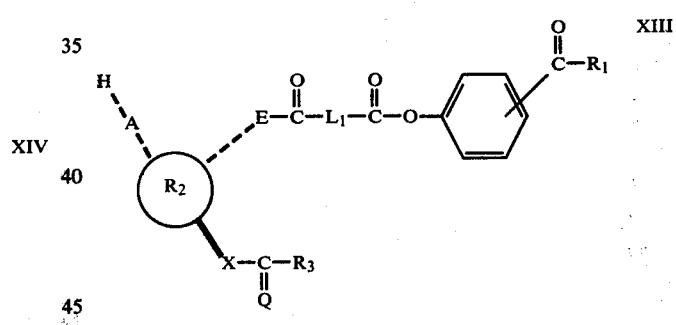
XIII
CHART D
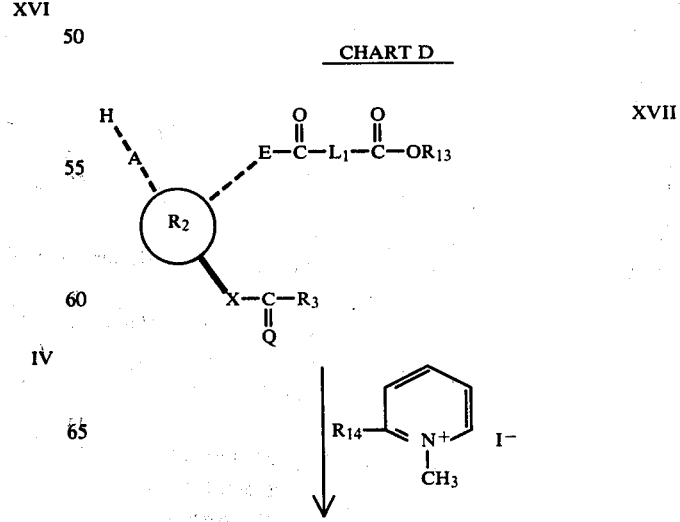
XVI
XVII
IV CHART D -continued

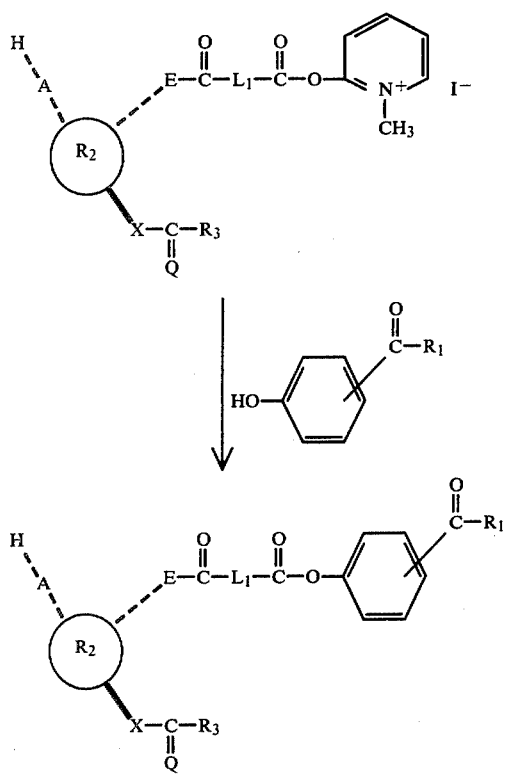

XIX

XIII (5Z)-3-oxa-PGI$_2$
(5Z)-11-deoxy-PGI$_2$
(5Z)-13,14-dihydro-PGI$_2$
(5Z)-13,14-dihydro-15-keto-PGI$_2$
(5Z)-13,14-didehydro-PGI$_2$
(5Z)-15-keto-PGI$_1$
(5Z)-15-deoxy-PGI$_2$
(5Z)-(15S)-15-methyl-PGI$_2$
(5Z)-16,16-dimethyl-PGI$_2$
(5Z)-16,16-difluoro-PGI$_2$
(5Z)-16-phenoxy-17,18,19,20-tetranor-PGI$_2$
(5Z)-17,18-didehydro-PGI$_2$
(5Z)-17-phenyl-18,19,20-trinor-PGI$_2$ Included are (5E)-PGI$_2$ analogs of copending U.S. patent application Ser. No. 912,552 filed June 5, 1978, for example:

(5E)-11-deoxy-PGI$_2$
(5E) (15S)-15-methyl-PGI$_2$
(5E)-16,16-dimethyl-PGI$_2$
(5E)-16,16-difluoro-PGI$_2$
(5E)-16-phenoxy-17,18,19,20-tetranor-PGI$_2$
(5E)-17-phenyl-18,19,20-trinor-PGI$_2$ Included are PGI$_1$ analogs, for which see Belg. Pat. No. 855,224, Derwent Farmdoc Abstract No. 86540Y, for example:

(6S or 6R)-PGI$_1$
(6S or 6R)-2-nor-PGI$_1$
(6S or 6R)-2,3-dinor-PGI$_1$
(6S or 6R)-2,3,4-trinor-PGI$_1$
(6S or 6R)-trans-$\Delta^2$-PGI$_1$
(6S or 6R)-trans-$\Delta^3$-PGI$_1$
(6S or 6R)-2,2-difluoro-13,14-dihydro-PGI$_1$
(6S or 6R)-3-oxa-PGI$_1$
(6S or 6R)-2,2-difluoro-16-phenoxy-17,18,19,20-tetranor-PGI$_1$
(6S or 6R)-trans-$\Delta^2$-16,16-dimethyl-PGI$_1$
(6S or 6R)-13,14-dihydro-PGI$_1$
(6S or 6R)-13,14-didehydro-PGI$_1$
(6S or 6R)-(15S)-15-methyl-PGI$_1$
(6S or 6R)-(15R)-16,16-dimethyl-PGI$_1$
(6S or 6R)-16-phenoxy-17,18,19,20-tetranor-PGI$_1$
(6S or 6R)-17-phenyl-18,19,20-trinor-PGI$_1$ Included are 6-hydroxy-PGI$_1$ analogs, for example:

6$\xi$-6-hydroxy-PGI$_1$
6$\xi$-6-hydroxy-2a,2b-dihomo-PGI$_1$
6$\xi$-6-hydroxy-11$\beta$-PGI$_1$
6$\xi$-6-hydroxy-11-deoxy-PGI$_1$
6$\xi$-6-hydroxy-13,14-dihydro-PGI$_1$
6$\xi$-6-hydroxy-13,14-didehydro-PGI$_1$
6$\xi$-6-hydroxy-15-keto-PGI$_1$
6$\xi$-6-hydroxy-(15S)-15-methyl-PGI$_1$
6$\xi$-6-hydroxy-(15R)-15-methyl-PGI$_1$
6$\xi$-6-hydroxy-(15S(-13,14-didehydro-PGI$_1$
6$\xi$-6-hydroxy-(15R)-13,14-didehydro-PGI$_1$
6$\xi$-6-hydroxy-16,16-dimethyl-PGI$_1$
6$\xi$-6-hydroxy-17,18-didehydro-PGI$_1$
6$\xi$-6-hydroxy-17-phenyl-18,19,20-trinor-PGI$_1$ Included are 9-deoxy-5,9$\alpha$-epoxy-$\Delta^4$-PGF$_1$ analogs, for example:

(4Z)-9-deoxy-5,9$\alpha$-epoxy-$\Delta^4$-PGF$_1$
(4Z)-9-deoxy-5,9$\alpha$-epoxy-$\Delta^4$-11-deoxy-PGF$_1$
(4Z)-9-deoxy-5,9$\alpha$-epoxy-$\Delta^4$-13,14-dihydro-PGF$_1$
(4Z)-9-deoxy-5,9$\alpha$-epoxy-$\Delta^4$-15-keto-PGF$_1$
(4Z)-9-deoxy-5,9$\alpha$-epoxy-$\Delta^4$-15-deoxy-PGF$_1$
(4Z)-9-deoxy-5,9$\alpha$-epoxy-$\Delta^4$-17-phenyl-18,19,20-trinor-PGF$_1$
(4Z)-9-deoxy-5,9$\alpha$-$\Delta^4$-13,14-didehydro-PGF$_1$
(4Z)-9-deoxy-5,9$\alpha$-epoxy-$\Delta^4$-(15S)-15-methyl-PGF$_1$
(4E)-9-deoxy-5,9$\alpha$-epoxy-$\Delta^4$-PGF$_1$ Included are 9-deoxy-5,9$\alpha$-epoxy-PGF$_1$ compounds of Belg. Pat. No. 860,278, Derwent Farmdoc Abstract No. 32096A, for example:

(5S or 5R)-9-deoxy-5,9$\alpha$-epoxy PGF$_1$
(5S or 5R)-9-deoxy-5,9$\alpha$-epoxy-(15S)-15-methyl-PGF$_1$
(5S or 5R)-9-deoxy-5,9$\alpha$-epoxy-(15R)-15-methyl-PGF$_1$
(5S or 5R)-9-deoxy-5,9$\alpha$-epoxy-16-phenoxy-17,18,19,20-tetranor-PGF$_1$
(5S or 5R)-9-deoxy-5,9$\alpha$-epoxy-2,3-dinor-(15S)-15-methyl-PGF$_1$
(2E, 5R)-9-deoxy-5,9$\alpha$-epoxy-$\Delta^2$-PGF$_1$ Included are 5-hydroxy-9-deoxy-5,9$\alpha$-epoxy-PGF$_1$ analogs for example:

5$\xi$-5-hydroxy-9-deoxy-5,9$\alpha$-epoxy-PGF$_1$
5$\xi$-5-hydroxy-9-deoxy-5,9$\alpha$-epoxy-11-deoxy-PGF$_1$
5$\xi$-5-hydroxy-9-deoxy-5,9$\alpha$-epoxy-13,14-dihydro-PGF$_1$ Included are 9-deoxy-6,9$\alpha$-epoxymethano-$\Delta^5$-PGF$_1$ analogs, for example:

(5Z)-9-deoxy-6,9$\alpha$-epoxymethano-$\Delta^5$-PGF$_1$
(5Z)-9-deoxy-6,9$\alpha$-epoxymethano-$\Delta^5$-11-deoxy-PGF$_1$ (5Z)-9-deoxy-6,9α-epoxymethano-Δ⁵-13,14-dihydro-PGF₁
(5Z)-9-deoxy-6,9α-epoxymethano-Δ⁵-13,14-didehydro-PGF₁
(5Z)-9-deoxy-6,9α-epoxymethano-Δ⁵-15-keto-PGF₁
(5Z)-9-deoxy-6,9α-epoxymethano-Δ⁵-15-deoxy-PGF₁
(5Z)-9-deoxy-6,9α-epoxymethano-Δ⁵-17,18-didehydro-PGF₁
(5Z)-9-deoxy-6,9α-epoxymethano-Δ⁵-17-phenyl-18,19,20-trinor-PGF₁
(5E)-9-deoxy-6,9α-epoxymethano-Δ⁵PGF₁

Included are 9-deoxy-6,9α-epoxymethano-PGF₁ analogs of Belg. Pat. No. 859,057, Derwent Farmdoc Abstract No. 25186A, for example:
(6S or 6R)-9-deoxy-6,9α-epoxymethano-PGF₁
(6S or 6R)-9-deoxy-6,9α-epoxymethano-2,3,4-trinor-PGF₁
(6S or 6R)-9-deoxy-6,9α-epoxymethano-2-homo-PGF₁
(6S or 6R)-9-deoxy-6,9α-epoxymethano-3-oxa-PGF₁
(6S or 6R)-9-deoxy-6,9α-epoxymethano-11-deoxy-PGF₁
(6S or 6R)-9-deoxy-6,9α-epoxymethano-(15S)-15-methyl-PGF₁
(6S or 6R)-9-deoxy-6,9α-epoxymethano-15-deoxy-PGF₁
(6S or 6R)-9-deoxy-6,9α-epoxymethano-16,16-dimethyl-PGF₁
(6S or 6R)-9-deoxy-6,9α-epoxymethano-16-phenoxy-17,18,19,20-tetranor-PGF₁
(6S or 6R)-9-deoxy-6,9α-epoxymethano-17-phenyl-18,19,20-trinor-PGF₁

Included are 6-hydroxy-9-deoxy-6,9α-epoxymethano-PGF₁ analogs, for example:
6ξ-6-hydroxy-9-deoxy-6,9α-epoxymethano-PGF₁
6ξ-6-hydroxy-9-deoxy-6,9α-epoxymethano-11β-PGF₁
6ξ-6-hydroxy-9-deoxy-6,9α-epoxymethano-11-deoxy-PGF₁
6ξ-6-hydroxy-9-deoxy-6,9α-epoxymethano-13,14-dihydro-PGF₁
6ξ-6-hydroxy-9-deoxy-6,9α-epoxymethano-13,14-didehydro-PGF₁
6ξ-6-hydroxy-9-deoxy-6,9α-epoxymethano-17,18-didehydro-PGF₁
6ξ-6-hydroxy-9-deoxy-6,9α-epoxymethano-17-phenyl-18,19,20-trinor-PGF.

III. Prostacyclin analogs of formula VII having a C-5-hydroxy or Δ⁴ feature, disclosed in copending U.S. patent application Ser. No. 815,648 filed July 14, 1977 now U.S. Pat. No. 4,110,532 and 821,541 filed Aug. 3, 1977 now U.S. Pat. No. 4,109,082.

Included are 5-hydroxy-PGI₁ analogs, for example:
(5S or 5R)-5-hydroxy-(6S)-PGI₁
(5S or 5R)-5-hydroxy-(6R)-PGI₁
(5S)-5-hydroxy-11-deoxy-11α-hydroxymethyl-(6S)-PGI₁
(5S)-5-hydroxy-11-deoxy-(6S)-PGI₁
(5S)-5-hydroxy-2-nor-7a-homo-(6S)-PGI₁
(5S or 5R)-5-hydroxy-(15S)-15-methyl-(6S)-PGI₁
(5S or 5R)-5-hydroxy-16,16-dimethyl-(6S)-PGI₁
(5R)-5-hydroxy-cis-13-(6S)-PGI₁
(5R)-5-hydroxy-13,14-didehydro-(6S)-PGI₁
(5R)-5-hydroxy-13,14-dihydro-(6S)-PGI₁
(5R)-5-hydroxy-2,2-difluoro-(6S)-PGI₁
(5R)-5-hydroxy-trans-Δ²-(6S)-PGI₁
(5R)-5-hydroxy-16-phenoxy-17,18,19,20-tetranor-(6S)-PGI₁
(5R)-5-hydroxy-17-phenyl-18,19,20-trinor-(6S)-PGI₁
(5R)-5-hydroxy-16,16-difluoro-(6S)-PGI₁

Included are trans-Δ⁴-PGI₁ analogs, for example:
trans-Δ⁴-(6R)-PGI₁
trans-Δ⁴-13,14-didehydro-(6R)-PGI₁
trans-Δ⁴-13,14-didehydro-(6R, 15R)-PGI₁
trans-Δ⁴-11-deoxy-11α-hydroxymethyl-(6S)-PGI₁
trans-Δ⁴-11-deoxy-(6S)-PGI₁
trans-Δ⁴-(6R)-9-deoxy-6,9α-epoxymethano-PGF₁
trans-Δ⁴-7a-homo-(6S)-PGI₁
trans-Δ⁴-cis-13-(6R)-PGI₁
trans-Δ⁴-13,14-dihydro-(6R)-PGI₁
trans-Δ⁴-13,14-dihydro-(15S)-15-methyl-(6R)-PGI₁
trans-Δ⁴-13,14-dihydro-16,16-dimethyl-(6R)-PGI₁
trans-66 ⁴-2,2-difluoro-13,14-dihydro-(15S)-15-methyl-(6R)-PGI₁
trans-Δ⁴-2,2,16,16-tetrafluoro-13,14-dihydro-(6R)-PGI₁
trans-Δ⁴-2,2-difluoro-(15S)-15-metjhyl-(6R)-PGI₁
trans-Δ⁴-2,2-difluoro-16,16-dimethyl-(6R)-PGI₁
trans-Δ⁴-2,2,16,16-tetrafluoro-(6R)-PGI₁
trans-Δ⁴-16-phenoxy-17,18,19,20-tetranor-(6R)-PGI₁
trans-Δ⁴-(15S)-15-methyl-(6R)-PGI₁
trans-Δ⁴-16,16-dimethyl-(6R)-PGI₁
trans-Δ⁴-16,16-difluoro-(6R)-PGI₁
trans-Δ⁴-11-deoxy-11α-hydroxymethyl-13,14-didehydro-(6S)-PGI₁
trans-Δ⁴-11-deoxy-13,14-didehydro-(6S)-PGI₁
trans-Δ⁴-(6R or 6S)-9-deoxy-6,9α-epoxymethano-13,14-didehydro-PGF₁
trans-Δ⁴-7a-homo-13,14-didehydro-(6R)-PGI₁
trans-Δ⁴-13,14-didehydro-(6S)-PGI₁
trans-Δ⁴-13,14-didehydro-(15S)-15-methyl-(6S)-PGI₁
trans-66 ⁴-13,14-didehydro-16,16-dimethyl-(6S)-PGI₁
trans-Δ⁴-13,14-didehydro-16,16-difluoro-(6S)-PGI₁
trans-Δ⁴-2,2-difluoro-13,14-didehydro-(6R)-PGI₁
trans-Δ⁴-13,14-didehydro-17-phenyl-18,19,20-trinor-(6R)-PGI₁
trans-Δ⁴-13,14-didehydro-16-phenoxy-17,18,19,20-tetranor-(6R)-PGI₁
trans-Δ⁴-13,14-didehydro-(15S)-15-methyl-(6R)-PGI₁
trans-Δ⁴-13,14-didehydro-16,16-dimethyl-(6R)-PGI₁
trans-Δ⁴-13,14-didehydro-16,16-difluoro-(6R)-PGI₁
trans-Δ⁴-13,14-didehydro-(6R)-PGI₁
trans,trans-Δ²,Δ⁴-11-deoxy-(6R)-PGI₁
trans,trans-Δ²,Δ⁴-(6R)-9-deoxy-6,9α-epoxymethano-PGF₁
trans,trans-Δ²,Δ⁴-7a-homo-(6R)-PGI₁
trans,trans-Δ²,Δ⁴-(6S)-PGI₁
trans,trans-Δ²,Δ⁴-(15S)-15-methyl-(6S)-PGI₁
trans,trans-Δ²,Δ⁴-16,16-dimethyl-(6S)-PGI₁
trans,trans-Δ²,Δ⁴-16,16-difluoro-(6S)-PGI₁
trans,trans-Δ²,Δ⁴-cis-13-(6R)-PGI₁
trans,trans-Δ²,Δ⁴-13,14-dihydro-(6R)-PGI₁
trans,trans-Δ²,Δ⁴-13,14-didehydro-(6R)-PGI₁ trans,trans-$\Delta^2,\Delta^4$-13,14-dihydro-(15S)-15-methyl-(6R)-PGI$_1$
trans,trans-$\Delta^2,\Delta^4$-13,14-dihydro-16,16-dimethyl-(6R)-PGI$_1$
trans,trans-$\Delta^2,\Delta^4$-(6R)-PGI$_1$
trans,trans-$\Delta^2,\Delta^4$-(15S)-15-methyl-(6R)-PGI$_1$
trans,trans-$\Delta^2,\Delta^4$-16,16-dimethyl-(6R)-PGI$_1$
trans,trans-$\Delta^2,\Delta^4$-16,16-difluoro-(6R)-PGI$_1$ IV. Prostacylin analogs of formula VIII having a C-6 alkoxy feature, disclosed in Belg. Pat. No. 851,122, Derwent Farmdoc Abstract No. 57511Y cited above, and including for example (6S or 6R)-6-methoxy-PGI$_1$ V. Prostacyclin analogs of formula IX having a C-4 oxo feature, disclosed in copending U.S. patent application Ser. No. 857,106, filed Dec. 5, 1977, issued as U.S. Pat. No. 4,126,744, including for example:

4-oxo-(6R or 6S)-PGI$_1$
4-oxo-cis-13-(6R or 6S)-PGI$_1$
4-oxo-13,14-didehydro-(6R or 6S)-PGI$_1$
4-oxo-7a-homo-(6R or 6S)-PGI$_1$
4-oxo-2a-homo-(6R or 6S)-PGI$_1$
4-oxo-(15S)-15-methyl-(6R or 6S)-PGI$_1$
4-oxo-16,16-difluoro-(6R or 6S)-PGI$_1$
4-oxo-17-phenyl-18,19,20-trinor-PGI$_1$.

VI. Prostacyclin analogs of formula X having a $\Delta^6$ feature, disclosed in copending U.S. patent application Ser. No. 860,673, filed Dec. 15, 1977, issued as U.S. Pat. No. 4,128,713 including for example:

$\Delta^6$-11-deoxy-11$\alpha$-11-hydroxymethyl-PGI$_1$
$\Delta^6$-13,14-didehydro-PGI$_1$
$\Delta^6$-13,14-didehydro-(15S)-15-methyl-PGI$_1$
$\Delta^6$-13,14-didehydro-16,16-dimethyl-PGI$_1$
$\Delta^6$-2,2-difluoro-13,14-didehydro-PGI$_1$
$\Delta^6$-2,2-difluoro-13,14-didehydro-(15S)-15-methyl-PGI$_1$
$\Delta^6$-cis-13-PGI$_1$
$\Delta^6$-13,14-didehydro-PGI$_1$
$\Delta^6$-13,14-dihydro-PGI$_1$
$\Delta^6$-13,14-dihydro-(15S)-15-methyl-PGI$_1$
$\Delta^6$-13,14-dihydro-16,16-dimethyl-PGI$_1$
$\Delta^6$-2,2-difluoro-13,14-dihydro-(15S)-15-methyl-PGI$_1$
$\Delta^6$-2,2,16,16-tetrafluoro-13,14-dihydro-PGI$_1$
$\Delta^6$-2,2-difluoro-(15S)-15-methyl-PGI$_1$
$\Delta^6$-2,2-difluoro-16,16-dimethyl-PGI$_1$
$\Delta^6$-2,2,16,16-tetrafluoro-PGI$_1$
$\Delta^6$-17-phenyl-18,19,20-trinor-PGI$_1$
$\Delta^6$-16-phenoxy-17,18,19,20-tetranor-PGI$_1$
$\Delta^6$-(15S)-15-methyl-PGI$_1$
$\Delta^6$-16,16-difluoro-PGI$_1$
$\Delta^6$-16,16-dimethyl-PGI$_1$
$\Delta^6$-PGI$_1$ VII. Prostacyclin analogs of formula XI having a $\Delta^7$ feature, disclosed in copending U.S. patent application Ser. No. 869,141, filed Jan. 13, 1978, including for example:

$\Delta^7$-6R or 6S)-PGI$_1$
$\Delta^7$-(6R or 6S)-11-deoxy-11$\alpha$-hydroxymethyl-PGI$_2$
$\Delta^7$-(6R or 6S)-11-deoxy-PGI$_1$
$\Delta^7$-(6R or 6S)-13,14-didehydro-PGI$_1$
$\Delta^7$-(6R or 6S)-13,14-didehydro-(15S)-15-methyl-PGI$_1$
$\Delta^7$-(6R or 6S)-13,14-didehydro-16,16-dimethyl-PGI$_1$
$\Delta^7$-(6R or 6S)-2a,2b-dihomo-(15S)-15-methyl-13,14-didehydro-PGI$_1$
$\Delta^7$-(6R or 6S)-cis-13-PGI$_1$
$\Delta^7$-(6R or 6S)-13,14-dihydro-PGI$_1$
$\Delta^7$-(6R or 6S)-13,14-dihydro-(15S)-15-methyl-PGI$_1$
$\Delta^7$-(6R or 6S)-13,14-dihydro-16,16-dimethyl-PGI$_1$
$\Delta^7$-2a,2b-dihomo-(6R or 6S)-13,14-dihydro-PGI$_1$
$\Delta^7$-2a,2b-dihomo-(6R or 6S)-13,14-dihydro-(15S)-15-methyl-PGI$_1$
$\Delta^7$-2a,2b-dihomo-(6R or 6S)-13,14-dihydro-16,16-difluoro-PGI$_1$
$\Delta^7$-2a,2b-dihomo-(6R or 6S)-(15S)-15-methyl-PGI$_1$
$\Delta^7$-2a,2b-dihomo-(6R or 6S)-16,16-dimethyl-PGI$_1$
$\Delta^7$-2a,2b-dihomo-(6R or 6S)-16,16-difluoro-PGI$_1$
$\Delta^7$-2a,2b-dihomo-(6R or 6S)-17-phenyl-18,19,20-trinor-PGI$_1$
$\Delta^7$-2a,2b-dihomo-(6R or 6S)-16-phenoxy-17,18,19,20-tetranor-PGI$_1$
$\Delta^7$-(6R or 6S)-(15S)-15-methyl-PGI$_1$
$\Delta^7$-(6R or 6S)-16,16-dimethyl-PGI$_1$
$\Delta^7$-(6R or 6S)-16,16-difluoro-PGI$_1$
$\Delta^7$-(6R or 6S)-16-phenoxy-17,18,19,20-tetranor-PGI$_1$
$\Delta^7$-(6R or 6S)-17-phenyl-18,19,20-trinor-PGI$_1$ VIII. Prostacyclin analogs of formula XII having a 6a-carba feature, disclosed in copending U.S. patent application Ser. No. 877,253, filed Feb. 13, 1978, including for example:

(5Z or 5E)-6a-carba-PGI$_2$
(5Z or 5E)-6a-carba-$\Delta^2$-PGI$_2$
(5Z or 6E)-6a-carba-(15S)-15-methyl-PGI$_2$
(5Z or 5E)-6a-carba-(15R)-15-methyl-PGI$_2$
(5Z or 5E)-6a-carba-16,16-dimethyl-PGI$_2$
(5Z or 5E)-6a-carba-2a,2b-dihomo-PGI$_2$
(5Z or 5E)-6a-carba-2a,2b-dihomo-(15S)-15-methyl-PGI$_2$
(5Z or 5E)-6a-carba-2a,2b-dihomo-16,16-dimethyl-PGI$_2$
(5Z or 5E)-6a-carba-2,2-difluoro-PGI$_2$
(5Z or 5E)-6a-carba-2,2-difluoro-(15S)-15-methyl-PGI$_2$
(5Z or 5E)-6a-carba-2,2-difluoro-16,16-dimethyl-PGI$_2$
(5Z or 5E)-6a-carba-11$\beta$-PGI$_2$
(5Z or 5E)-6a-carba-11-deoxy-PGI$_2$
(5Z or 5E)-6a-carba-11-dehydro-PGI$_2$
(5Z or 5E)-6a-carba-13,14-dihydro-PGI$_2$
(5Z or 5E)-6a-carba-13,14-dihydro-(15S)-15-methyl-PGI$_2$ Referring again to Chart A, the formula-XV mixed anhydride is formed readily at temperatures in the range $-40°$ to $+60°$ C. preferably at $-10°$ to $+10°$ C. so that the rate is reasonably fast and yet side reactions are minimized. The isobutylchloroformate reagent is preferably used in excess, for example 1.2 molar equivalents up to 4.0 per mole of the PG compound. The reaction is preferably done in a solvent and for this purpose acetone is preferred, although other relatively non-polar solvents are used such as acetonitrile, dichloromethane, and chloroform. The reaction is run in the presence of a tertiary amine, for example triethylamine, and the coformed amine hydrochloride usually crystallizes out, but need not be removed for the next step.

The anhydride is usually not isolated but is reacted directly in solution with the phenol, preferably in the presence of a tertiary amine such as pyridine or triethylamine.

The acyl-substituted phenols used in preparing the formula-IV esters are known in the art or readily available by methods known in the art. Herein the term "phenol" refers to any of these acyl-substituted phenols.

The phenol is preferably used in equivalent amounts or in excess to insure that all of the mixed anhydride is converted to ester. Excess phenol is separated from the product by methods described herein or known in the art, for example by crystallization. The tertiary amine is not only a basic catalyst for the esterification but also a convenient solvent. Other examples of tertiary amines useful for this purpose include N-methylmorpholine, triethylamine, diisopropylethylamine, and dimethylaniline. 2-Methylpyridine and quinoline result in a slow reaction. A highly hindered amine such as 2,6-dimethyllutidine is not useful because of the slowness of the reaction.

The reaction with the anhydride proceeds smoothly at room temperature (about 20° to 30° C.) and can be followed in the conventional manner with thin layer chromatography (TLC), usually being found complete within 1–4 hours.

The reaction mixture is worked up to yield the ester following methods known in the art, and the product is purified, for example by silica gel chromatography.

Solid esters are converted to a free-flowing crystalline form on crystallization from a variety of solvents, including ethyl acetate, tetrahydrofuran, methanol, and diethyl ether, by cooling or evaporating a saturated solution of the ester in the solvent or by adding a miscible non-solvent such as hexane, or water. The crystals are then collected by conventional techniques, e.g., filtration or centrifugation, washed with a small amount of solvent, and dried under reduced pressure. They may also be dried in a current of warm nitrogen or argon, or by warming to about 75° C. Although the crystals are normally pure enough for many applications, they may be recrystallized by the same general techniques to achieve improved purity after each re-crystallization.

For those prostacyclin-like compounds which contain an enol ether linkage like $PGI_2$ it is preferred that the extractions be done in the presence of a small amount (2%) of a trialkylamine.

Chart B shows a second method of preparing these formula-IV esters, by way of a pyridinium ester intermediate of formula XVI. The method has been applied to other carboxylic esters by T. Mukaiyama, et al., Chemistry Letters 1975, pp. 1045–1048. The reagent, a 2-halo-1-methyl-pyridinium iodide, is known or readily available. As to the 2-bromo compound, see for example G. B. Barlin, et al., J. Chem. Soc., Perkins Trans., 2 (1974) 790.

The 2-halo-1-methyl-pyridinium iodide is preferably used in equivalent amount or in excess. The tertiary amine is used in equivalent amount or in excess for an alkali metal salt or in double that amount for the free acid of the prostacyclin-type compound. Useful tertiary amines are those named above for the Chart A reaction, including triethylamine.

The reaction with the 2-halo-1-methyl-pyridinium iodide proceeds smoothly at room temperature (about 20° to 30° C.) and can be carried out at temperatures up to about 120° C. The reaction is conveniently run in an solvent such as toluene, methylene chloride, dimethoxyethane, pyridine, or dimethylformamide.

The resulting pyridinium ester (XVI) is usually not isolated but is reacted directly in solution with the phenol, preferably in the presence of a tertiary amine such as was used in the first step.

The reaction mixture is worked up by conventional methods including two-phase extraction, silica gel column chromatography, and crystallization. For those prostacyclin-like compounds which contain an enol ether linkage like $PGI_2$ it is preferred that the extractions be done in the presence of a small amount (2%) of a trialkylamine.

The 2-halo-pyridinium salt method is preferred for those prostacyclin-type compounds like $PGI_2$ which are unstable in the acid form and are accordingly available as salts, generally the sodium salt.

Charts C and D illustrate the processes used for the 6-(and 5-) keto compounds of formula XVII which also form acyl-substituted phenyl esters according to this invention. Chart C corresponds to Chart A and follows the same procedures described above for Chart A. Likewise Chart D corresponds to Chart B.

Instead of the 6 (or 5)-keto-$PGF_{1\alpha}$ compound as starting compound as in Charts C and D, the acyl-substituted phenyl ester of an appropriate prostacyclin ($PGI_2$)-type compound or analog may optionally serve as the starting material of the corresponding 6 (or 5)-keto-$PGF_{1\alpha}$ ester compound, carrying out the transformation in solution in the presence of a mild acid such as aqueous potassium hydrogen sulfate. There is then recovered the corresponding phenyl ester of the 6 (or 5)-keto-$PGF_{1\alpha}$ compound.

Sources of the 6-keto-$PGF_{1\alpha}$ analogs of formula XVII wherein A is —O—(oxa) or —$CH_2$O— wherein —$CH_2$ is bonded to $R_2$ and wherein E is —$CH_2$— are the same sources reported above for 6-hydroxy-$PGI_1$ analogs. The two types of compounds are isomers and are readily isomerized in solution. See Belg. Pat. No. 851,122 for example. Corresponding 6-keto-$PGF_{1\alpha}$ analogs are, for example:

6-keto-$PGF_{1\alpha}$
6-keto-trans-$\Delta^2$-$PGF_{1\alpha}$
6-keto-2a,2b-dihomo-$PGF_{1\alpha}$
6-keto-2,2-difluoro-$PGF_{1\alpha}$
6-keto-11$\beta$-$PGF_{1\alpha}$
6-keto-11-deoxy-$PGF_{1\alpha}$
6-keto-13,14-dihydro-$PGF_{1\alpha}$
6-keto-13,14-didehydro-$PGF_{1\alpha}$
6-keto-15-deoxy-$PGF_{1\alpha}$
6,15-diketo-$PGF_{1\alpha}$
6-keto-(15S)-15-methyl-$PGF_{1\alpha}$
6-keto-(15R)-15-methyl-$PGF_{1\alpha}$
6-keto-13,14-didehydro-(15S)-$PGF_{1\alpha}$
6-keto-13,14-didehydro-(15R)-$PGF_{1\alpha}$
6-keto-16,16-dimethyl-$PGF_{1\alpha}$
6-keto-16,16-difluoro-$PGF_{1\alpha}$
6-keto-17,18-didehydro-$PGF_{1\alpha}$
6-keto-17-phenyl-18,19,20-trinor-$PGF_{1\alpha}$
6-keto-16-phenoxy-17,18,19,20-tetranor-$PGF_{1\alpha}$
6-keto-9-deoxy-9$\alpha$-hydroxymethyl-$PGF_1$
6-keto-9-deoxy-9$\alpha$-hydroxymethyl-11$\beta$-$PGF_1$
6-keto-9,11-dideoxy-9$\alpha$-hydroxymethyl-$PGF_1$
6-keto-9-deoxy-9$\alpha$-hydroxymethyl-13,14-dihydro-$PGF_1$ 6-keto-9-deoxy-9α-hydroxymethyl-13,14-didehydro-PGF$_1$
6-keto-9-deoxy-9α-hydroxymethyl-17,18-didehydro-PGF$_1$
6-keto-9-deoxy-9α-hydroxymethyl-17-phenyl-18,19,20-trinor-PGF$_1$ The source of the 5-keto-PGF$_{1\alpha}$ analogs of formula XVII wherein A is —O— (oxa) and E is —CH$_2$CH$_2$— is the source reported above for the 5-hydroxy-9-deoxy-5,9α-epoxy-PGF$_1$ analogs. These two types of compounds are isomers and are readily isomerized. Corresponding 5-keto-PGF$_{1\alpha}$-analogs are, for example:

5-keto-PGF$_{1\alpha}$
5-keto-11-deoxy-PGF$_{1\alpha}$
5-keto-13,14-dihydro-PGF$_{1\alpha}$
5-keto-13,14-didehydro-PGF$_{1\alpha}$
5-keto-(15S)-15-methyl-PGF$_{1\alpha}$
5-keto-17-phenyl-18,19,20-trinor-PGF$_{1\alpha}$.

DESCRIPTION OF THE PREFERRED EMBODIMENTS

The invention is illustrated by, but not limited to, the following examples.

All temperatures are in degrees centigrade.

Melting points as reported are uncorrected.

Infrared absorption spectra are recorded on a Perkin-Elmer model 421 infrared spectrophotometer. Except when specified otherwise, undiluted (neat) samples are used.

The NMR spectra are recorded on a Varian A60, A-60D, T-60 or XL-100 spectrophotometer in deuterochloroform solutions with tetramethylsilane as an internal standard.

Mass spectra are recorded on a Varian Model MAT CH7 Mass Spectrometer, a CEC Model 110B Double Focusing High Resolution Mass Spectrometer, or a LKB Model 9000 Gas Chromatograph-Mass Spectrometer (ionization voltage 22 or 70 ev.), and samples are usually run as TMS (trimethylsilyl) derivatives.

"Brine", herein, refers to an aqueous saturated sodium chloride solution.

"R$_f$", as used herein is a term in thin layer chromatography referring to the ratio between the movement of a spot of the sample and that of the solvent front.

"More polar" and "less polar" refer to the difference in mobility on TLC silica gel plates or on a silica gel column of two compounds. The members of a pair of isomers may be distinguished as "more polar" or "less polar" isomers, considering that mobility. The faster-moving compound in chromatography is, of course, the less polar one.

"Florisil ®", herein is a chromatographic magnesium silicate produced by the Floridin Co. See Fieser, et al., "Reagents for Organic Synthesis" p. 393 John Wiley and Sons, Inc., New York, N.Y. (1967).

"Skellysolve B", herein, refers to mixed isomeric hexanes.

"TLC", herein refers to thin layer chromatography.

"Concentrating", as used herein, refers to concentration under reduced pressure, preferably at less than 50 mm. and at temperatures below 35° C.

"Drying", as used herein, refers to contacting a compound, in solution, with an anhydrous agent such as sodium sulfate or magnesium sulfate to remove water and filtering to remove solids.

Silica gel chromatography, as used herein, is understood to include elution, collection of fractions, and combination of those fractions shown by TLC to contain the desired product free of starting material and impurities.

Preparation 1

11-Deoxy-Δ$^{10}$-PGI$_2$, Methyl Ester

I. There is first prepared 11-deoxy-Δ$^{10}$-PGF$_{2\alpha}$, methyl ester by reducing PGA$_2$, methyl ester. A solution of PGA$_2$, methyl ester (2.0 g.) in 10 ml. of tetrahydrofuran is treated at about 0° C. with 20 ml. of 0.5 M 9-borabicyclo[3.3.1]nonane in tetrahydrofuran, with stirring. After 3 hours further stirring, the mixture is treated with 2 ml. of methanol and concentrated. The residue is taken up in 20 ml. of diethyl ether-Skellysolve B (isomeric hexanes) (1:1) containing about 0.3 ml. of ethanolamine. The mixture is stirred, filtered, and concentrated to an oil. The oil is chromatographed under pressure on 230–400 mesh silica gel, eluting with ethyl acetate (40–60%)-Skellysolve B, to give 1.6 g. of mixed 9α- and 9β-hydroxy compounds. The mixture is again chromatographed, eluting with acetone (20–40%)-methylene chloride to give 11-deoxy-Δ$^{10}$-PGF$_{2\alpha}$, methyl esters, 0.53 g., having R$_f$ 0.39 (TLC on silica gel in ethyl acetate-cyclohexane (1:1)), and NMR peaks at 5.88, 5.48, 4.63, 4.05, 3.65, 3.05, and 0.9δ. More polar material, 1.01 g., is also obtained, consisting of the 9β isomer.

II. Next is prepared 5ξ-iodo-9,11-dideoxy-6,9α-epoxy-Δ$^{10}$-PGF$_{1\alpha}$, methyl ester:

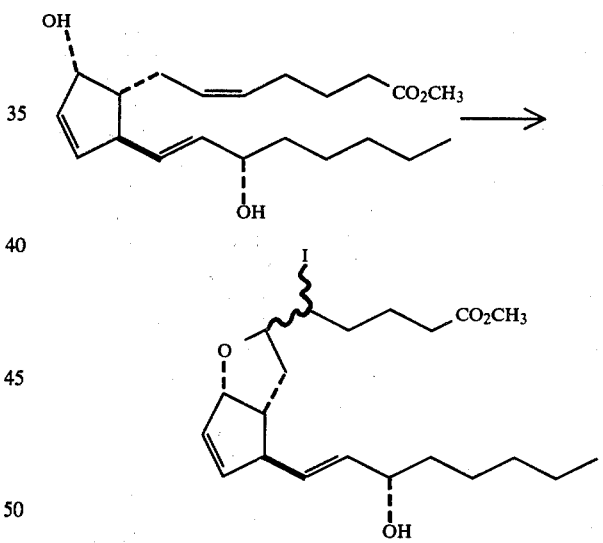

a mixture of the compound of I above (0.45 g.), 10 ml. of methylene dichloride, and 15 ml. of saturated aqueous sodium bicarbonate is treated at about 0° C. with portions of a solution of iodine (0.35 g.) in 25 ml. of methylene chloride during 40 min. The mixture is stirred an additional 10 min., then the organic phase is separated, washed with aqueous sodium sulfite until colorless, washed with brine, dried, and concentrated to an oil, 0.64 g. The iodo compound has R$_f$ 0.52 and 0.48 (TLC on silica gel in ethyl acetate-cyclohexane (1:1)), and NMR peaks at 5.78, 5.5, 5.2, 4.5, 4.05, 3.67 and 0.9δ.

III. The title compound is obtained as follows. A solution of the product of II above (0.32 g.) in 5 ml. of toluene is treated with 0.6 ml. of 1,5-diazabicyclo[5.4.-0]undecene-5 warmed to 45° C., stirred at 45° for 6 hr., and left at about 25° C. for 36 hr. Ice and water are added, and the organic phase is separated, dried over magnesium sulfate in the presence of a few drops of triethylamine, and concentrated. The residue is chromatographed, eluting with ethyl acetate (10–20%)-Skellysolve B-0.25% triethylamine, to yield the title compound, 0.10 g., having $R_f$ 0.56 (TLC on silica gel in ethyl acetate-cyclohexane (1:1)), NMR peaks at 5.83, 5.5, 5.34, 3.8–4.3 3.63, 3.0–3.6, and 0.9$\delta$, infrared absorption at 3460, 1740, 1695, 1665, 1630, 1245, 1200, 1170, 1130, 1050, 1025, and 970 cm$^{-1}$, and high resolution mass spectral line at 420.2673.

Preparation 2

11-Deoxy-$\Delta^{10}$-PGI$_2$, Sodium Salt

A solution of the methyl ester (Preparation 1, 0.11 g.) in 5 ml. of methanol is treated with 0.15 g. of sodium carbonate in 2.5 ml. of water at about 25° C. for 2.5 days. The mixture is filtered, concentrated to remove methanol, and diluted with two volumes of acetonitrile. The organic phase is separated, further diluted with 50 ml. of acetonitrile containing a few drops of triethylamine, concentrated, taken up in water-triethylamine, and lyophilized. The resulting glassy solid of the title compound, 0.7 g., has infrared absorption at 3500, 1710, 1575, 1045, 1015, 970, and 925 cm$^{-1}$.

Preparation 3

11-Deoxy-$\Delta^{10}$-(6RS)-PGI$_1$, Methyl Ester

A solution of 5$\xi$-iodo-9,11-dideoxy-6,9$\alpha$-epoxy-$\Delta^{10}$-PGF$_{1\alpha}$, methyl ester (Preparation 1, 0.32 g.) in 5 ml. of ethanol and 0.3 ml. of tributyltin chloride is treated at about 25° C. with a solution of 0.1 g. of sodium borohydride in 4 ml. of ethanol during 15 min. The mixture is stirred one hr., acidified with dilute hydrochloric acid, concentrated to remove ethanol, diluted with brine, and extracted with ethyl acetate. The organic phase is washed with brine, dried, and concentrated. The oily residue is chromatographed, eluting with ethyl acetate (20–40%)-Skellysolve B to yield the title compounds, 0.14 g., having $R_f$ 0.61 (TLC on silica gel in ethyl acetate-cyclohexane (1:1)), NMR peaks at 5.77, 5.55, 5.18, 3.8–4.25, 3.63, 3.1 and 0.9$\delta$, infrared absorption of 3440, 1740, 1625, 1245, 1200, 1175, 1050, 1025, and 975 cm$^{-1}$, and high resolution mass spectral line at 422.2852.

EXAMPLE 1

PGI$_2$, 4-Acetylphenyl Ester

Two methods are described.

I. Refer to Chart A (mixed anhydride method). A stirred suspension of PGI$_2$ sodium salt (0.187 G.) in 15 ml. of methylene chloride and 0.120 g. of triethylamine is treated at about 0° C. with isobutylchloroformate (0.0656 g.) in 1 ml. of methylene chloride. The mixture is stirred at about 25° C. for 2 hr., then cooled again to about 0° C. and treated with 4-hydroxyacetophenone (0.0653 g.) in 1 ml. of methylene chloride containing about 0.25 ml. of triethylamine. The mixture is stirred at about 25° C. for one hr., cooled to 0° C., diluted with 25 ml. of a mixture of methylene chloride-triethylamine (95:5), washed with 5% aqueous sodium bicarbonate and cold 0.1 N potassium hydroxide. The organic phase is dried and concentrated to the title compound, 0.131 g. Crystals are obtained from diethyl ether containing a trace of triethylamine, 0.063 g., m.p. 72°–78° C., which are further purified by chromatography on Florisil ®.

II. Refer to Chart B (2-halo-pyridinium salt method). A solution of PGI$_2$ sodium salt (1.00 g.) in 35 ml. of dimethylformamide and 0.352 g. of triethylamine is treated with 2-bromo-1-methyl-pyridinium iodide (J. Chem. Soc., Perkins Trans., 2 (1974) 790) (0.801 g.) at about 25° C. for one hr. The mixture is then treated with 4-hydroxyacetophenone (0.364 g.) in 2 ml. of dimethylformamide and 0.4 g. of triethylamine at about 25° C. The mixture is stirred about 16 hr., then poured into ice-water containing 4 ml. of 1 N potassium hydroxide and extracted with diethyl ether. The organic phase is washed with cold 0.02 N potassium hydroxide, dried, and concentrated to the title compound. Crystals are obtained from diethyl ether containing about 0.25% of triethylamine, to yield 0.355 g. m.p. 77°–80° C. An analytical sample is obtained on recrystallization, 0.255 g., m.p. 83°–84° C., having $R_f$ 0.35 (TLC on silica gel in ethyl acetate), NMR peaks at 7.98, 7.18, 5.63–5.33, 4.75–3.34, 2.95–1.08, 2.56, and 0.87 $\delta$, infrared absorption at 3400, 2950, 1770, 1690, 1600, 1500, 1410, 1350, 1260, 1200, 1160, 1110, 1045, 965, 910, 850, and 730 cm$^{-1}$, and high resolution mass spectral line (for bis-trimethylsilyl derivative) 614.3450.

Following the procedures of Example 1 but replacing the 4-hydroxyacetophenone of that example with the following phenols there are obtained the corresponding acyl-substituted phenyl esters of prostacyclin (PGI$_2$):

(2 or 3)-hydroxyacetophenone
(2, 3 or 4)-hydroxypropiophenone
(2, 3 or 4)-hydroxybutyrophenone
(2, 3 or 4)-hydroxy(2-methylpropio)phenone
(2, 3 or 4)-hydroxyvalerophenone
(2, 3 or 4)-hydroxy(3-methylbutyro)phenone
4-hydroxy(2,2-dimethyl propio)phenone, namely the
(2 or 3)-acetylphenyl
(2, 3 or 4)-propionylphenyl
(2, 3 or 4)-butyrylphenyl
(2, 3 or 4)-isobutyrylphenyl
(2, 3 or 4)-valerylphenyl
(2, 3 or 4)-isovalerylphenyl and
4-pivalylphenyl
esters of PGI$_2$.

Following the procedures of Example 1 as set forth in Charts A and B, but replacing the PGI$_2$ sodium salt with the sodium, potassium or lithium salt of (5E)-prostacyclin and each of the formula-V-XII compounds named above, all within the scope of formula XIV, there are obtained the corresponding 4-acetylphenyl esters of those named compounds.

Likewise following the procedures of Example 1, now referring to Charts C and D, but replacing the PGI$_2$ sodium salt with the free acid, sodium, potassium, or lithium salt of each of the formula-XVII 6 (or 5)-keto-PGF$_{1\alpha}$ named above, there are obtained the corresponding 4-acetylphenyl esters of those named compounds.

EXAMPLE 2

PGI$_1$, 4-Acetylphenyl Ester

Refer to Chart A. A solution of PGI$_1$ (1.00 g.) in 15 ml. of methylene chloride and 0.566 g. of triethylamine is treated at about 25° C. with isobutylchloroformate (0.389 g.) and stirred for 20 min. Then 4-hydroxyacetophenone (0.388 g.) is added and the mixture stirred for 2 hr. It is then diluted with methylene chloride, washed with water, 0.1 N. potassium hydroxide, and brine, dried and concentrated to yield an oil, 1.6 g. The mixture is chromatographed, eluting with ethyl acetate, to yield the title compound, 1.0 g., m.p. 89°–91°

C., having NMR peaks at 8.00, 7.18, 5.72–5.40, 4.66–3.34, 3.18, 2.83–1.05, 2.58, and 0.88 δ, and infrared absorption at 3420, 2900, 1760, 1660, 1600, 1460, 1410, 1360, 1320, 1270, 1210, 1165, 1140, 1050, 1020, 970, 920, 850, and 730 cm$^{-1}$.

EXAMPLE 3

16,16-Dimethyl-PGI$_1$, 4-Acetylphenyl Ester.

Refer to Chart A. A mixture of 16,16-dimethyl-PGI$_1$ (1.00 g.) and triethylamine (0.535 g.) in 15 ml. of methylene dichloride is treated at about 25° C. with isobutylchloroformate (0.391 g.). After 20 min. there is added 4-hydroxyacetophenone (0.389 g.) in 2 ml. of methylene chloride together with about 0.2 g. triethylamine. After one hr. there is added 120 ml. of methylene chloride, and the mixture is washed with 0.1 N. aqueous potassium hydroxide, water, and brine, then dried and concentrated. Chromatography, eluting with acetone-methylene chloride (1:3), yields the title compound, an oil, 1.07 g., having R$_f$0.27 (TLC on silica gel in acetone-methylene chloride (1:3), NMR peaks at 8.02, 7.22, 5.97–5.45, 4.66–3.33, 3.02–1.06, 2.58, 0.88, and 0.84 δ, and infrared absorption at 3500, 2950, 2875, 1760, 1675, 1590, 1490, 1460, 1400, 1340, 1250, 1200, 1160, 1010, 965, 845, and 725 cm$^{-1}$.

EXAMPLE 4

(6R)-16,16-Difluoro-PGI$_1$, 4-Acetylphenyl Ester.

Refer to Chart A. Following the procedures of Example 3, but using (6R)-16,16-difluoro-PGI$_1$, (0.30 g.) in 5 ml. methylene dichloride with 0.14 g. of triethylamine, then adding 0.11 g. of isobutylchloroformate and finally 0.11 g. of 4-hydroxyacetophenone, there is obtained after work-up an oil, 0.35 g. The oil is chromatographed, eluting with acetone (10–30%)-methylene dichloride to yield the title compound, 0.29 g., having R$_f$0.27 (TLC on silica gel in ethyl acetatecyclohexane (4:1)), NMR peaks at 8.1–7.9, 7.4–7.1, 5.85–5.6, 2.6, and 0.88 δ, and mass spectral lines at 652, 562, 545, 537, and 517.

EXAMPLE 5

16-Phenoxy-17,18,19,20-tetranor-PGI$_1$, 4-Acetylphenyl Ester.

Refer to Chart A. A solution of 16-phenoxy-17,18,19,20-tetranor-PGI$_1$ (0.30 g.) in 5 ml. of methylene chloride and 0.14 g. of triethylamine is treated with isobutylchloroformate (0.11 g.) at about 25° C. for 0.5 hr. There is then added 4-hydroxyacetophenone (0.11 g.) and the mixture is stirred at about 25° C. for 1.5 hr. The mixture is diluted with 30 ml. of methylene chloride, washed with water, 0.1 N sodium hydroxide and brine, dried, and concentrated to yield the title compound, 0.35 g. Chromatography yields 0.30 g. which is crystallized from diethyl ether, 0.257 g., m.p. 93.8°–94.9° C., having R$_f$ 0.21 (TLC on silica gel in acetone-methylene chloride (3:7)), and mass spectral peaks (TMS derivative) at 545.2730, 558, 455, 429, and 209.

EXAMPLE 6

(5S)-9-Deoxy-5,9α-epoxy-PGF$_1$, 4-Acetylphenyl Ester.

Refer to Chart A. A solution of (5S)-9-deoxy-5,9α-epoxy-PGF$_1$ (0.354 g.) in 5 ml. of methylene chloride containing 0.202 g. of triethylamine is treated at about 25° C. with isobutylchloroformate (0.137 g.) and stirred for 0.5 hr. There is then added 0.137 g. of 4-hydroxyacetophenone and stirring is continued for 4 hr. The mixture is diluted with 75 ml. of methylene chloride, washed with water, 0.1 N aqueous sodium hydroxide, water, and brine, dried, and concentrated to yield an oil, 0.387 g. The oil is chromatographed, eluting with acetone (25–30%)-hexane, to yield an oil, 0.313 g., m.p. 91.0°–91.5° C. (recrystallized from diethyl ether-pentane, m.p. 91.5°–92.0° C.) having R$_f$0.35 (TLC on silica gel in acetone (30%)-hexane), and NMR peaks at 8.05, 7.2, 5.5, 3.9, 3.3, 2.65, and 0.89 δ.

EXAMPLE 7

6-Keto-PGF$_{1α}$, 4-Acetylphenyl Ester

A mixture of PGI$_2$ sodium salt (0.561 g.) in triethylamine (0.200 g.) in 15 ml. of dimethylformamide is treated at about 25° C. with 0.45 g. of solid 2-bromo-1-methyl-pyridinium iodide and stirred for 1.2 hr. There is then added a solution of 4-hydroxyacetophenone (0.204 g.) in 1 ml. of dimethylformamide followed by about 0.20 ml. of triethylamine. After standing overnight there is observed one major spot on TLC. The mixture is treated with 5 ml. of 2 N. aqueous potassium hydrogen sulfate and within 15 min. the mixture contains a more polar material as shown by TLC. After further stirring for 1.5 hr. the mixture is poured into 70 ml. of ice-water and extracted with diethyl ether. The organic phase is washed with brine, dried, and concentrated to an oil, 0.680 g. The oil is chromatographed, eluting with ethyl acetate, to obtain the title compound, 0.175 g. having R$_f$0.25 (TLC on silica gel in ethyl acetate) and NMR peaks at 8.05, 7.29, 5.72–5.40, 4.83–3.50, 3.50–3.02, 3.02–1.08, 2.58, and 8.89 δ.

I claim:

1. An acid ester of prostacyclin of the formula

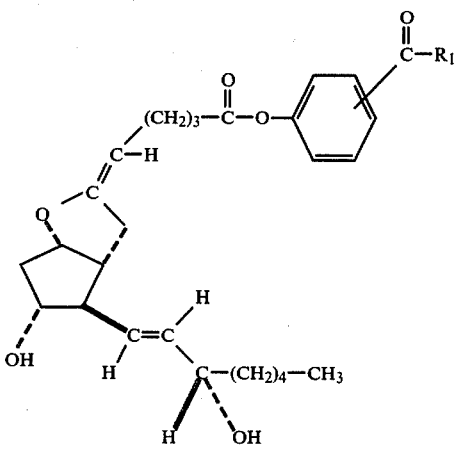

or its (5E) isomer, wherein R$_1$ is alkyl of one to 4 carbon atoms, inclusive, with the proviso that when R$_1$ is tert-butyl the group

is only in the 4-position.

2. Prostacyclin, 4-acetylphenyl ester, a compound according to claim 1.

3. Prostacyclin, 3-acetylphenyl ester, a compound according to claim 1.

4. Prostacyclin, 2-acetylphenyl ester, a compound according to claim 1.

5. Prostacyclin, 4-propionylphenyl ester, a compound according to claim 1.

6. Prostacyclin, 4-butyrylphenyl ester, a compound according to claim 1.

7. Prostacyclin, 4-isobutyrylphenyl ester, a compound according to claim 1.

8. Prostacyclin, 4-valerylphenyl ester, a compound according to claim 1.

9. Prostacyclin, 4-isovalerylphenyl ester, a compound according to claim 1.

10. Prostacyclin, 4-pivalylphenyl ester, a compound according to claim 1.

11. (5E)-Prostacyclin, 4-acetylphenyl ester, a compound according to claim 1.

12. An acid ester of a prostacyclin analog of the formula

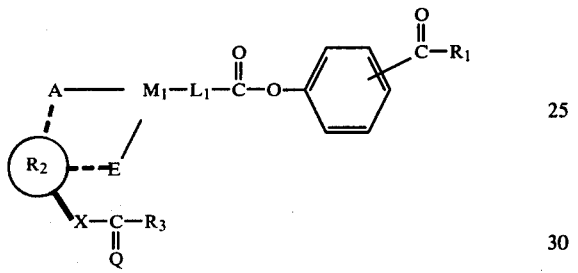

wherein A is (1) —O— (oxa) or, when E is —CH$_2$—, (2) —CH$_2$—O—, with —CH$_2$ bonded to (R$_2$)
wherein E is —CH$_2$— or —CH$_2$CH$_2$—,
wherein L$_1$ is
(1) —(CH$_2$)$_n$— wherein n is one to 5, inclusive,
(2) —(CH$_2$)$_p$—CF$_2$— wherein p is 2, 3, or 4, or
(3) —(CH$_2$)$_v$—CH=CH— wherein v is 1, 2, or 3,
wherein M$_1$ is

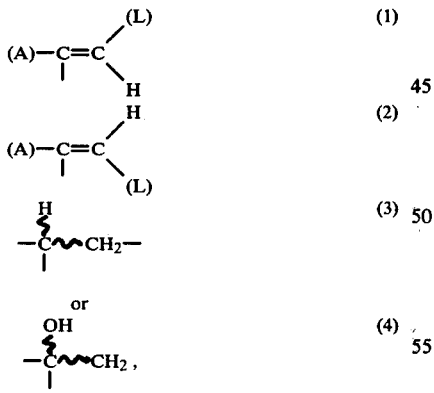

where ~ indicates attachment in alpha or beta configuration,
wherein Q is

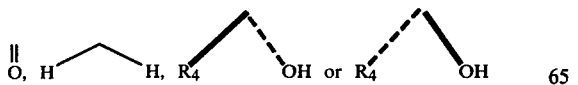

wherein R$_4$ is hydrogen or alkyl of one to 4 carbon atoms, inclusive, wherein R$_1$ is alkyl of one to 4 carbon atoms, inclusive, with the proviso that when R$_1$ is tert-butyl the —C(O)—R$_1$ group is in the 4-position,
wherein (R$_2$) is

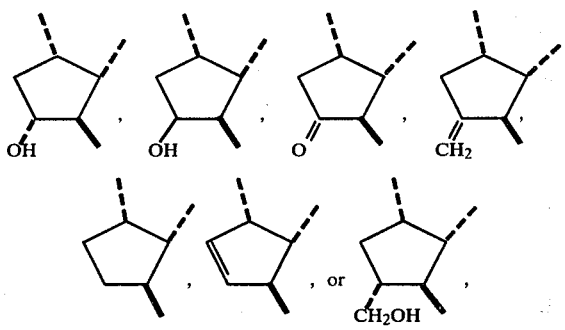

wherein R$_3$ is

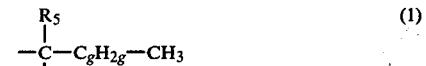

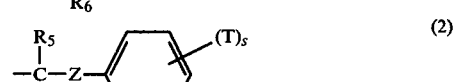

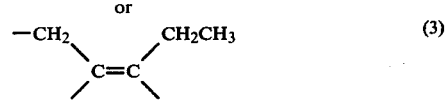

wherein C$_g$H$_{2g}$ is alkylene of one to 9 carbon atoms, inclusive, with one to 5 carbon atoms, inclusive, in the chain between —CR$_5$R$_6$— and terminal methyl, wherein R$_5$ and R$_6$ are hydrogen, alkyl of one to 4 carbon atoms, inclusive, or fluoro, being the same or different, with the proviso that one of R$_5$ and R$_6$ is fluoro only when the other is hydrogen or fluoro and the further proviso that neither R$_5$ nor R$_6$ is fluoro when Z is oxa (—O—);

wherein Z represents an oxa atom (—O—) or C$_j$H$_{2j}$ wherein C$_j$H$_{2j}$ is a valence bond or alkylene of one to 9 carbon atoms, inclusive, with one to 6 carbon atoms, inclusive between CR$_5$R$_6$— and the phenyl ring;

wherein T is alkyl of one to 4 carbon atoms; inclusive, fluoro, chloro, trifluoromethyl, or —OR$_7$— wherein R$_7$ is alkyl of one to 4 carbon atoms, inclusive, and s is zero, one, 2 or 3, with the proviso that not more than two T's are other thn alkyl and when s is 2 or 3 the T's are either the same or different, and wherein X is
(1) trans-CH=CH—
(2) cis-CH=CH—
(3) —C≡C— or
(4) —CH$_2$CH$_2$— with the proviso that said formula does not include prostacyclin or its (5E) isomer.

13. (5Z)-trans-Δ$^2$-PGI$_2$, 4-acetylphenyl ester, a compound according to claim 12.

14. (5Z)-2,2-Difluoro-PGI$_2$, 4-acetylphenyl ester, a compound according to claim 12.

15. (5Z)-11-Deoxy-PGI$_2$, 4-acetylphenyl ester, a compound according to claim 12.

16. (5Z)-13,14-Dihydro-PGI$_2$, 4-acetylphenyl ester, a compound according to claim 12.

17. (5Z)-13,14-Didehydro-PGI$_2$, 4-acetylphenyl ester, a compound according to claim 12.

18. (5Z)-15-Deoxy-PGI$_2$, 4-acetylphenyl ester, a compound according to claim 12.

19. (5Z)-(15S)-15-Methyl-PGI$_2$, 4-acetylphenyl ester, a compound according to claim 12.

20. (5Z)-16,16-Dimethyl-PGI$_2$, 4-acetylphenyl ester, a compound according to claim 12.

21. (5Z)-16,16-Difluoro-PGI$_2$, 4-acetylphenyl ester, a compound according to claim 12.

22. (5Z)-16-Phenoxy-17,18,19,20-tetranor-PGI$_2$, 4-acetylphenyl ester, a compound according to claim 12.

23. (5Z)-17,18-Didehydro-PGI$_2$, 4-acetylphenyl ester, a compound according to claim 12.

24. (5Z)-17-Phenyl-18,19,20-trinor-PGI$_2$, 4-acetylphenyl ester, a compound according to claim 12.

25. (5E)-11-Deoxy-PGI$_2$, 4-acetylphenyl ester, a compound according to claim 12.

26. (5E)-16,16-Dimethyl-PGI$_2$, 4-acetylphenyl ester, a compound according to claim 12.

27. (5E)-16,16-Difluoro-PGI$_2$, 4-acetylphenyl ester, a compound according to claim 12.

28. (5E)-16-Phenoxy-17,18,19,20-tetranor-PGI$_2$, 4-acetylphenyl ester, a compound according to claim 12.

29. (5E)-17-Phenyl-18,19,20-trinor-PGI$_2$, 4-acetylphenyl ester, a compound according to claim 12.

30. (6S and 6R)-PGI$_1$, 4-acetylphenyl ester, compounds according to claim 12.

31. (6S and 6R)-Trans-$\Delta^2$-PGI$_1$, 4-acetylphenyl ester, compounds according to claim 12.

32. (6S and 6R)-2,2-Difluoro-13,14-dihydro-PGI$_1$, 4-acetylphenyl ester, compounds according to claim 12.

33. (6S and 6R)-2,2-Difluoro-16-phenoxy-17,18,19,20-tetranor-PGI$_1$, 4-acetylphenyl ester, compounds according to claim 12.

34. (6S and 6R)-2,2-Difluoro-13,14-dihydro-17-phenyl-18,19,20-trinor-PGI$_1$, 4-acetylphenyl ester, compounds according to claim 12.

35. (6S and 6R)-Trans-$\Delta^2$-16,16-dimethyl-PGI$_1$, 4-acetylphenyl ester, compounds according to claim 12.

36. (6S and 6R)-13,14-Dihydro-PGI$_1$, 4-acetylphenyl ester, compounds according to claim 12.

37. (6S and 6R)-13,14-Didehydro-PGI$_1$, 4-acetylphenyl ester, compounds according to claim 12.

38. (6S and 6R)-(15S)-15-methyl-PGI$_1$, 4-acetylphenyl ester, compounds according to claim 12.

39. (6S and 6R)-(15R)-15-methyl-PGI$_1$, 4-acetylphenyl ester, compounds according to claim 12.

40. (6S and 6R)-16,16-Dimethyl-PGI$_1$, 4-acetylphenyl ester, compounds according to claim 12.

41. (6S and 6R)-16,16-Difluoro-PGI$_1$, 4-acetylphenyl ester, compounds according to claim 12.

42. (6S and 6R)-16-Phenoxy-17,18,19,20-tetranor-PGI$_1$, 4-acetylphenyl ester, compounds according to claim 12.

43. 6$\epsilon$-6-Hydroxy-PGI$_1$, 4-acetylphenyl ester, a compound according to claim 12.

44. (4Z)-9-Deoxy-5,9$\alpha$-epoxy-$\Delta^4$-PGF$_1$, 4-acetylphenyl ester, a compound according to claim 12.

45. (4Z)-9-Deoxy-5,9$\alpha$-epoxy-$\Delta^4$-17-phenyl-18,19,20-trinor-PGF$_1$, 4-acetylphenyl ester, a compound according to claim 12.

46. (4Z)-9-Deoxy-5,9$\alpha$-epoxy-$\Delta^4$-13,14-didehydro-PGF$_1$, 4-acetylphenyl ester, a compound according to claim 12.

47. (4Z)-9-Deoxy-5,9$\alpha$-epoxy-$\Delta^4$-(15S)-15-methyl-PGF$_1$, 4-acetylphenyl ester, a compound according to claim 12.

48. (4E)-9-Deoxy-5,9$\alpha$-epoxy-$\Delta^4$-PGF$_1$, 4-acetylphenyl ester, a compound according to claim 12.

49. (5S and 5R)-9-Deoxy-5,9$\alpha$-epoxy-PGF$_1$, 4-acetylphenyl ester, compounds according to claim 12.

50. (5S and 5R)-9-Deoxy-5,9$\alpha$-epoxy-(15S)-15-methyl-PGF$_1$, 4-acetylphenyl ester, compounds according to claim 12.

51. (5S and 5R)-9-Deoxy-5,9$\alpha$-epoxy-(15R)-15-methyl-PGF$_1$, 4-acetylphenyl ester, compounds according to claim 12.

52. (2E, 5R)-9-Deoxy-5,9$\alpha$-epoxy-$\Delta^2$-PGF$_1$, 4-acetylphenyl ester, a compound according to claim 12.

53. (5Z)-9-Deoxy-6,9$\alpha$-epoxymethano-$\Delta^5$-PGF$_1$, 4-acetylphenyl ester, a compound according to claim 12.

54. (5Z)-9-Deoxy-6,9$\alpha$-epoxymethano-$\Delta^5$-13,14-didehydro-PGF$_1$, 4-acetylphenyl ester, a compound according to claim 12.

55. (5E)-9-Deoxy-6,9$\alpha$-epoxymethano-$\Delta^5$-PGF$_1$, 4-acetylphenyl ester, a compound according to claim 12.

56. (6S and 6R)-9-Deoxy-6,9$\alpha$-epoxymethano-PGF$_1$, 4-acetylphenyl ester, compounds according to claim 12.

57. (6S and 6R)-9-Deoxy-6,9$\alpha$-epoxymethano-11-deoxy-PGF$_1$, 4-acetylphenyl ester, compounds according to claim 12.

58. (6S and 6R)-9-Deoxy-6,9$\alpha$-epoxymethano-(15S)-15-methyl-PGF$_1$, 4-acetylphenyl 59. (6S and 6R)-9-Deoxy-6,9$\alpha$-epoxymethano-16,16-dimethyl-PGF$_1$, 4-acetylphenyl ester, compounds according to claim 12.

60. (6S and 6R)-9-Deoxy-6,9$\alpha$-epoxymethano-16-phenoxy-17,18,19,20-tetranor-PGF$_1$, 4-acetylphenyl ester, compounds according to claim 12.

61. (6S and 6R)-9-Deoxy-6,9$\alpha$-epoxymethano-17-phenyl-18,19,20-trinor-PGF$_1$, 4-acetylphenyl ester, compounds according to claim 12.

62. An acid ester of a prostacyclin analog of the formula

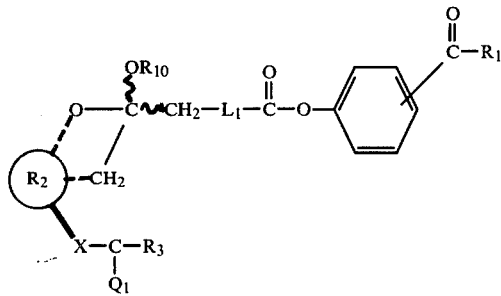

wherein L$_1$ is (1) —(CH$_2$)$_n$— wherein n is one to 5, inclusive,
(2) —(CH$_2$)$_p$—CF$_2$— wherein p is 2, 3, or 4, or
(3) —(CH$_2$)$_v$—CH=CH— wherein v is 1, 2, or 3, wherein Q is

wherein R$_4$ is hydrogen or alkyl of one to 4 carbon atoms, inclusive, wherein R$_1$ is alkyl of one to 4 carbon atoms, inclusive, with the proviso that when R$_1$ is tert-butyl the group $$-\overset{O}{\underset{\|}{C}}-R_1$$

is in the 4-position, wherein (R$_2$) is

[structures of substituted cyclopentane rings with OH, OH, =O, =CH$_2$, (unsubstituted), cyclopentene, and CH$_2$OH substituents]

wherein R$_3$ is $$-\overset{R_5}{\underset{R_6}{\overset{|}{\underset{|}{C}}}}-C_gH_{2g}-CH_3 \quad (1)$$

$$-\overset{R_5}{\underset{R_6}{\overset{|}{\underset{|}{C}}}}-Z-\text{[phenyl ring with (T)}_s\text{]} \quad (2)$$

or $$\begin{array}{c}-CH_2\\ \phantom{-CH_2}\diagdown\\ \phantom{-CH_2}C=C\\ H\phantom{-CH_2}\diagup\phantom{xx}\diagdown H\end{array}\begin{array}{c}\phantom{x}\\ CH_2CH_3\\ \phantom{x}\\ \phantom{x}\end{array} \quad (3)$$

wherein C$_g$H$_{2g}$ is alkylene of one to 9 carbon atoms, inclusive, with one to 5 carbon atoms, inclusive, in the chain between —CR$_5$R$_6$— and terminal methyl, wherein R$_5$ and R$_6$ are hydrogen, alkyl of one to 4 carbon atoms, inclusive, or fluoro, being the same or different, with the proviso that one of R$_5$ and R$_6$ is fluoro only when the other is hydrogen or fluoro and the further proviso that neither R$_5$ nor R$_6$ is fluoro when Z is oxa (—O—);

wherein Z represents an oxa atom (—O—) or C$_j$H$_{2j}$ wherein C$_j$H$_{2j}$ is a valence bond or alkylene of one to 9 carbon atoms, inclusive, with one to 6 carbon atoms, inclusive between CR$_5$R$_6$— and the phenyl ring;

wherein T is alkyl of one to 4 carbon atoms; inclusive, fluoro, chloro, trifluoromethyl, or —OR$_7$— wherein R$_7$ is alkyl of one to 4 carbon atoms, inclusive, and s is zero, one, 2 or 3, with the proviso that not more than two T's are other than alkyl and when s is 2 or 3 the T's are either the same or different, wherein R$_{10}$ is straight-chain alkyl of one to 6 carbon atoms, inclusive, wherein X is
(1) trans-CH=CH—
(2) cis-CH=CH—
(3) —C≡C— or
(4) —CH$_2$CH$_2$—, and wherein ~ indicates attachment in cis or trans configuration.

63. (6S and 6R)-6-Methoxy-PGI$_1$, 4-acetylphenyl ester, compounds according to claim 62.

* * * * *

UNITED STATES PATENT OFFICE
CERTIFICATE OF CORRECTION

Patent No. 4,180,657     Dated  25 December 1979

Inventor(s)  John C. Sih

It is certified that error appears in the above-identified patent and that said Letters Patent are hereby corrected as shown below:

In the Abstract, that portion of the formula reading

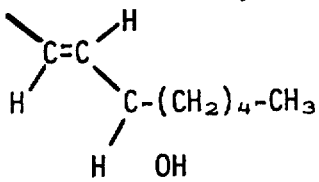   should read   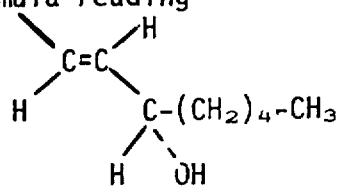

Column 1, lines 38-48, the formula should read as follows:

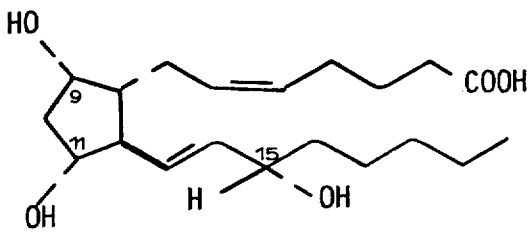

Column 20, line 20, "trans-66 $^4$-2,2-difluoro-" should read -- trans-$\Delta^4$-2,2-difluoro- --; line 25, "-15-metjhyl-" should read -- -15-methyl- --; line 40, "trans-66 $^4$-13,14-didehydro-" should read -- trans-$\Delta^4$-13,14-didehydro- --;

Column 24, line 36, "bonded to $R_2$ " should read -- bonded to (R₂) --;

Column 27, line 24, "0.7 g" should read -- 0.07 g --;

Column 33, line 62, "6ε-6-Hydroxy-PGI$_1$" should read -- 6ξ-6-Hydroxy-PGI$_1$ --;

Column 34, lines 48-58, that portion of the formula reading

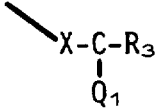   should read   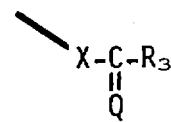

UNITED STATES PATENT OFFICE
CERTIFICATE OF CORRECTION

Patent No. 4,180,657   Dated 25 December 1979

Inventor(s) John C. Sih

It is certified that error appears in the above-identified patent and that said Letters Patent are hereby corrected as shown below:

Column 35, lines 22-27,

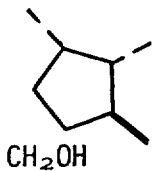   should read   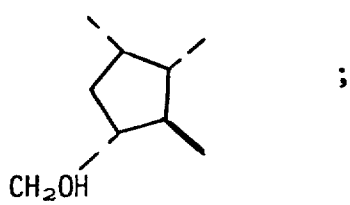 ;

Column 36, line 35, "-C=C-" should read -- -C≡C- --.

Signed and Sealed this

Eighteenth Day of August 1981

[SEAL]

Attest:

Attesting Officer

GERALD J. MOSSINGHOFF

Commissioner of Patents and Trademarks